(12) United States Patent
Ishihara et al.

(10) Patent No.: US 12,303,099 B2
(45) Date of Patent: *May 20, 2025

(54) SURGICAL SYSTEM AND METHOD OF DISPLAYING INFORMATION IN THE SAME

(71) Applicant: MEDICAROID CORPORATION, Kobe (JP)

(72) Inventors: Kazuki Ishihara, Kobe (JP); Kenichiro Tsurumoto, Kyoto (JP); Yuki Suzuki, Kyoto (JP); Masaya Kunimoto, Kyoto (JP); Yuki Kimpara, Kyoto (JP); Yuichi Kageyama, Kyoto (JP)

(73) Assignee: MEDICAROID CORPORATION, Kobe (JP)

( * ) Notice: Subject to any disclaimer, the term of this patent is extended or adjusted under 35 U.S.C. 154(b) by 1222 days.

This patent is subject to a terminal disclaimer.

(21) Appl. No.: 16/817,618

(22) Filed: Mar. 13, 2020

(65) Prior Publication Data

US 2020/0205916 A1 Jul. 2, 2020

Related U.S. Application Data

(63) Continuation of application No. 16/576,716, filed on Sep. 19, 2019, now Pat. No. 11,478,313.

(30) Foreign Application Priority Data

Sep. 25, 2018 (JP) .................. 2018-179273

(51) Int. Cl.
| | | |
|---|---|---|
| A61B 1/00 | (2006.01) | |
| A61B 1/05 | (2006.01) | |
| A61B 18/12 | (2006.01) | |
| A61B 34/00 | (2016.01) | |
| A61B 34/35 | (2016.01) | |
| A61B 90/00 | (2016.01) | |

(Continued)

(52) U.S. Cl.
CPC ............ *A61B 1/00042* (2022.02); *A61B 1/05* (2013.01); *A61B 18/1206* (2013.01);
(Continued)

(58) Field of Classification Search
CPC ... A61B 1/00042; A61B 1/05; A61B 1/00009; A61B 34/25; A61B 34/35; A61B 90/361;
(Continued)

(56) References Cited

U.S. PATENT DOCUMENTS

| | | |
|---|---|---|
| 6,728,599 B2 | 4/2004 | Wang et al. |
| 8,418,073 B2 | 4/2013 | Mohr et al. |

(Continued)

FOREIGN PATENT DOCUMENTS

| | | |
|---|---|---|
| JP | 2016-000360 A | 1/2016 |
| JP | 2017-512554 A | 5/2017 |

(Continued)

*Primary Examiner* — Michael J Carey
*Assistant Examiner* — William B Chou
(74) *Attorney, Agent, or Firm* — METROLEX IP LAW GROUP, PLLC; Robert L. Scott, Esq.

(57) ABSTRACT

A surgical system according to one or more embodiments may include: manipulators respectively supporting an endoscope and first and second surgical instruments; a remote control apparatus including a display device, a first operation handle for right hand to operate the first surgical instrument, and a second operation handle for left hand to operate the second surgical instrument; and a control apparatus. The control apparatus may display, on the display device, a graphical user interface, overlapped with the image captured by the endoscope, the graphical user interface including a first area that displays information on the first surgical instrument to be operated by the first operation handle, a second area that displays information on the second surgical instrument to be operated by the second operation handle, and a third area that displays information on the endoscope, which are arranged side by side in order from right to left.

20 Claims, 13 Drawing Sheets

(51) Int. Cl.
*A61B 17/00* (2006.01)
*A61B 18/00* (2006.01)
*A61B 18/14* (2006.01)
*A61B 34/30* (2016.01)

(52) U.S. Cl.
CPC .............. *A61B 34/25* (2016.02); *A61B 34/35* (2016.02); *A61B 90/361* (2016.02); *A61B 90/37* (2016.02); *A61B 1/00009* (2013.01); *A61B 2017/00477* (2013.01); *A61B 2017/00973* (2013.01); *A61B 2018/00589* (2013.01); *A61B 2018/00601* (2013.01); *A61B 2018/0063* (2013.01); *A61B 2018/1253* (2013.01); *A61B 2018/126* (2013.01); *A61B 18/1482* (2013.01); *A61B 2034/301* (2016.02)

(58) Field of Classification Search
CPC . A61B 90/37; A61B 18/1206; A61B 18/1482; A61B 2034/301; A61B 2017/00477; A61B 2017/00973; A61B 2018/00589; A61B 2018/00601; A61B 2018/0063; A61B 2018/1253; A61B 2018/126
See application file for complete search history.

(56) References Cited

U.S. PATENT DOCUMENTS

| | | |
|---|---|---|
| 2006/0167440 A1 | 7/2006 | Cooper et al. |
| 2007/0197896 A1 | 8/2007 | Moll et al. |
| 2010/0228249 A1 | 9/2010 | Mohr et al. |
| 2010/0228264 A1 | 9/2010 | Robinson et al. |
| 2011/0196199 A1* | 8/2011 | Donhowe ............... A61B 5/065 600/102 |
| 2011/0306830 A1* | 12/2011 | Bechtold ................ A61B 1/041 600/109 |
| 2012/0078043 A1* | 3/2012 | Miyayashiki ...... A61B 1/00045 600/109 |
| 2014/0012081 A1* | 1/2014 | Juergens ............ A61B 1/00174 600/109 |
| 2014/0171959 A1 | 6/2014 | Yacono |
| 2014/0357947 A1* | 12/2014 | Fujitani .............. A61B 1/00006 600/104 |
| 2016/0166336 A1* | 6/2016 | Razzaque .............. A61B 90/37 606/130 |
| 2017/0164869 A1* | 6/2017 | Lee ........................ A61B 34/20 |
| 2017/0172675 A1 | 6/2017 | Jarc et al. |
| 2018/0221100 A1 | 8/2018 | Berry et al. |
| 2019/0254631 A1* | 8/2019 | Yoshimura ............... A61B 8/12 |
| 2019/0339836 A1 | 11/2019 | Kanda |
| 2020/0069160 A1* | 3/2020 | Oosake ........... A61B 1/000094 |
| 2020/0100857 A1* | 4/2020 | Nakashima ................ B25J 3/04 |
| 2021/0204802 A1* | 7/2021 | Nir ......................... G02B 13/06 |

FOREIGN PATENT DOCUMENTS

| | | |
|---|---|---|
| WO | 2011/125007 A1 | 10/2011 |
| WO | 2018/096987 A1 | 5/2018 |
| WO | 2018/170031 A1 | 9/2018 |

* cited by examiner

FIG. 15 CUTTING PEDAL (OPERATION PREPARATION POSITION) SCREEN
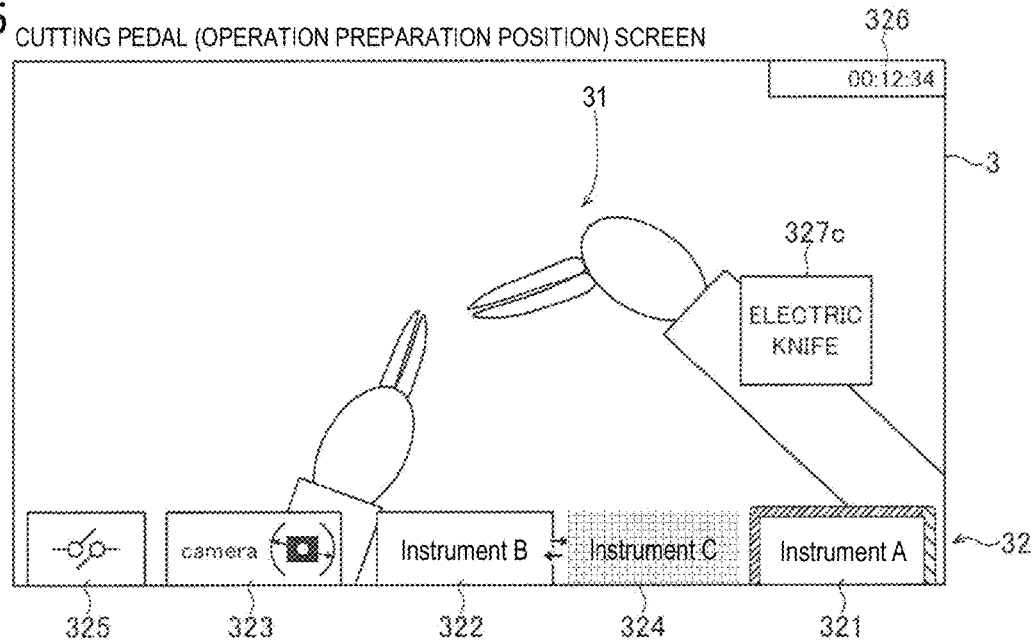
FIG. 16 CUTTING PEDAL (RIGHT) (OPERATION) SCREEN
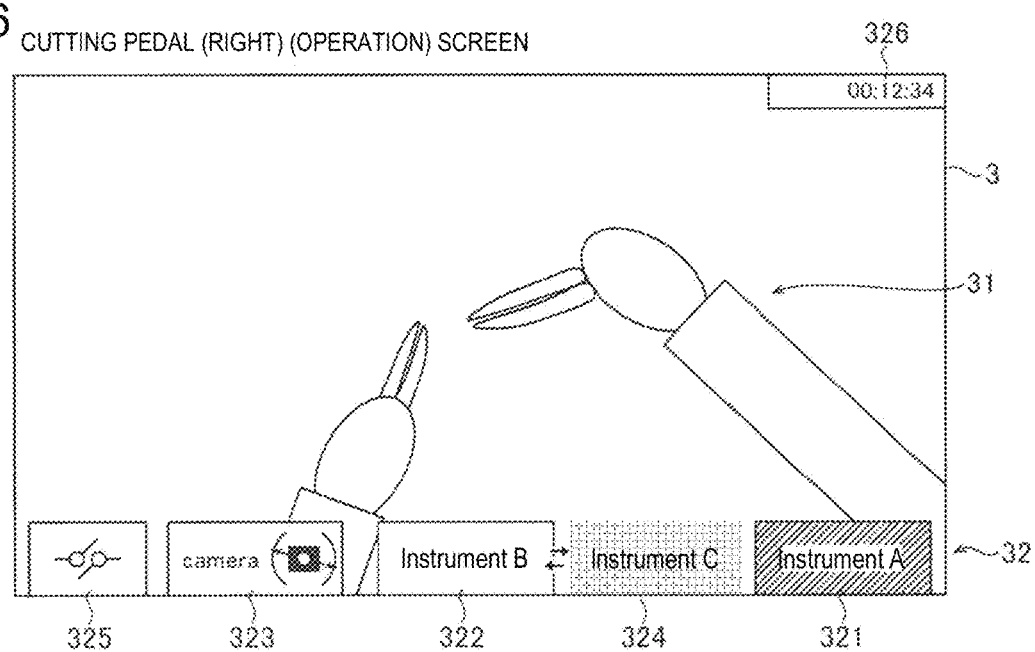

SURGICAL SYSTEM AND METHOD OF DISPLAYING INFORMATION IN THE SAME

CROSS REFERENCE TO RELATED APPLICATIONS

This application is a continuation of application Ser. No. 16/576,716, filed on Sep. 19, 2019, which is based upon and claims the benefit of priority from the prior Japanese Patent Application No. 2018-179273, filed on Sep. 25, 2018, the entire contents of all of which are incorporated herein by reference.

BACKGROUND

The disclosure may relate to a surgical system, and may particularly relate to a surgical system including a remote control apparatus for operating surgical instruments.

In a related art, there has been known a surgical system including a remote control apparatus for operating surgical instruments (e.g., see Document 1).

Document 1 discloses a surgical system that includes: manipulators that support an endoscope for capturing images of the surgery site and surgical instruments; a display device that displays the images captured by the endoscope; and a remote control apparatus that includes an operation handle for right hand and an operation handle for left hand to remotely operate the surgical instruments. The surgical system is configured to display information on a surgical instrument operated by the right hand-operation handle in a lower right end region of the display device, to display information on a surgical instrument operated by the left hand-operation handle in a lower left end region of the display device, and to display information on the endoscope in an upper central end region of the display device.

Document 1: U.S. Pat. No. 8,418,073

SUMMARY

As described above, the surgical system displays the information on the surgical instrument operated by the right hand-operation handle in the lower right end region of the display device, displays the information on the surgical instrument operated by the left hand-operation handle in the lower left end region of the display device, and displays the information on the endoscope in the upper central end region of the display device. Since the information on the surgical instruments and the information on the endoscope are separately displayed on the upper end and the lower end, the operator is required to move the eyes a lot to check the pieces of information on the surgical instruments and endoscope supported by the manipulators. This may lead to a problem of degradation of the visibility of the information on the surgical instruments and endoscope supported by the manipulators.

An object of one or more embodiments of the disclosure may be to provide a surgical system that is capable of suppressing degradation of the visibility of information on surgical instruments and an endoscope supported by manipulators.

A first aspect of one or more embodiments may be a surgical system that includes: manipulators that respectively support an endoscope, a first surgical instrument, and a second surgical instrument; a remote control apparatus that includes a display device that displays an image captured by the endoscope, a first operation handle for right hand to operate the first surgical instrument, and a second operation handle for left hand to operate the second surgical instrument; and a control apparatus that controls at least the display device. The control apparatus displays, on the display device, a graphical user interface overlapped with the image captured by the endoscope, the graphical user interface including a first area that displays information on the first surgical instrument to be operated by the first operation handle, a second area that displays information on the second surgical instrument to be operated by the second operation handle, and a third area that displays information on the endoscope, which are arranged side by side in order from right to left.

A second aspect of one or more embodiments may be a surgical system that includes: manipulators that respectively support an endoscope, a first surgical instrument, and a second surgical instrument; a remote control apparatus that includes a display device that displays an image captured by the endoscope, a first operation handle for right hand to operate the first surgical instrument, a second operation handle for left hand to operate the second surgical instrument, and an operation pedal section including foot pedals; and a control apparatus that controls at least the display device. The operation pedal section includes a first foot pedal to execute a function of the first surgical instrument, a second foot pedal to execute a function of the second surgical instrument, and a third foot pedal to execute a function of the endoscope. The control apparatus displays a graphical user interface, overlapped with the image captured by the endoscope, on the display device, the graphical user interface including a first area that displays information on the first surgical instrument to be operated by the first operation handle, a second area that displays information on the second surgical instrument to be operated by the second operation handle, and a third area that displays information on the endoscope, which are arranged in the same order as the arrangement order of the first foot pedal, the second foot pedal, and the third pedal on the operation pedal section.

A third aspect of one or more embodiments may be a method of displaying information in a surgical system. The surgical system may include: manipulators that respectively support an endoscope, a first surgical instrument, and a second surgical instrument; and a remote control apparatus that includes a display device that displays an image captured by the endoscope, a first operation handle for right hand to operate the first surgical instrument, and a second operation handle for left hand to operate the second surgical instrument. The method may include: generating a graphical user interface including a first area that displays information on the first surgical instrument to be operated by the first operation handle, a second area that displays information on the second surgical instrument to be operated by the second operation handle, and a third area that displays information on the endoscope, which are arranged side by side in order from right to left; and displaying the generated graphical user interface, overlapped with the image captured by the endoscope, on the display device.

A fourth aspect of one or more embodiments may be a method of displaying information in a surgical system. The surgical system may include: manipulators that respectively support an endoscope, a first surgical instrument, and a second surgical instrument; and a remote control apparatus that includes a display device that displays an image captured by the endoscope, a first operation handle for right hand to operate the first surgical instrument, a second operation handle for left hand to operate the second surgical instrument, and an operation pedal section including foot pedals, wherein the operation pedal section includes a first foot pedal to execute a function of the first surgical instrument, a second foot pedal to execute a function of the second surgical instrument, and a third foot pedal to execute a function of the endoscope. The method may include: generating a graphical user interface including a first area that displays information on the first surgical instrument to be operated by the first operation handle, a second area that displays information on the second surgical instrument to be operated by the second operation handle, and a third area that displays information on the endoscope, which are arranged in the same order as the arrangement order of the first foot pedal, the second foot pedal, and the third pedal on the operation pedal section; and displaying the generated graphical user interface, overlapped with the image captured by the endoscope, on the display device.

BRIEF DESCRIPTION OF DRAWINGS

FIG. 15 is a diagram illustrating a view of an example of a screen of the display device when a foot is at an operation preparation position for a cutting pedal (right) according to an embodiment;

FIG. 16 is a diagram illustrating a view of an example of a screen of the display device when the cutting pedal (right) is operated according to an embodiment;

DETAILED DESCRIPTION

Figure 1:
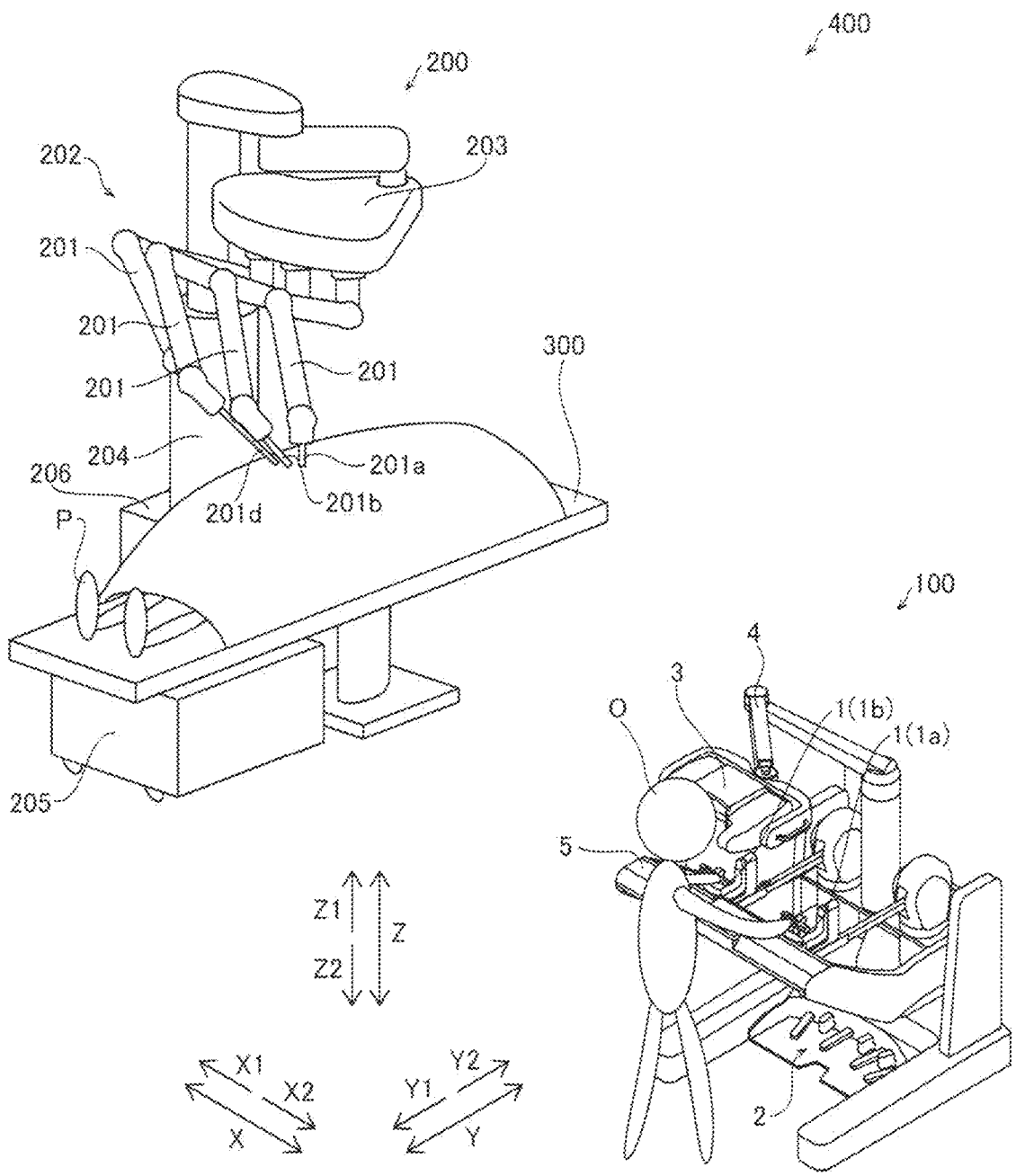
FIG. 1 is a diagram illustrating an overview of a surgical system according to an embodiment.

Descriptions are provided hereinbelow for one or more embodiments based on the drawings. In the respective drawings referenced herein, the same constituents are designated by the same reference numerals and duplicate explanation concerning the same constituents is omitted. All of the drawings are provided to illustrate the respective examples only.

(Configuration of Surgical System)

A configuration of a surgical system 400 according to one or more embodiments is described with reference to FIGS. 1 to 21.

As illustrated in FIG. 1, the surgical system 400 includes a remote control apparatus 100 and a patient-side apparatus 200. The remote control apparatus 100 is provided for teleoperation of medical equipment included in the patient-side apparatus 200. When an operator O, as a surgeon, inputs an action mode instruction to be executed by the patient-side apparatus 200 to the remote control apparatus 100, the remote control apparatus 100 transmits the action mode instruction to the patient-side apparatus 200 through a controller 206. In response to the action mode instruction transmitted from the remote control apparatus 100, the patient-side apparatus 200 operates medical equipment, such as surgical instruments 201*a* to 201*c* and an endoscope 201*d*, attached to manipulators 201. This allows for minimally invasive surgery.

The patient-side apparatus 200 constitutes an interface to perform a surgery for a patient P. The patient-side apparatus 200 is placed beside an operation table 300 on which the patient P lies. The patient-side apparatus 200 includes the manipulators 201. One of the manipulators 201 supports the endoscope 201*d* while the others hold the surgical instruments 201*a* to 201*c*. The manipulators 201 are commonly supported by a platform 203. Each of the manipulators 201 includes joints. Each joint includes a driver including a servo-motor and a position detector such as an encoder. The manipulators 201 are configured so that the medical equipment attached to each manipulator 201 is controlled by a driving signal given through the controller 206, to perform a desired movement.

The platform 203 is supported by a positioner 202 placed on the floor of an operation room. The positioner 202 includes a column 204 and a base 205. The column 204 includes an elevating shaft adjustable in the vertical direction. The base 205 includes wheels and is movable on the floor surface.

The surgical instruments 201a to 201c as the medical equipment are detachably attached to the tip of three of the four manipulators 201, respectively. The surgical instruments 201a to 201c each include a housing, a shaft, and an end effector. The housing is attached to the corresponding one of the manipulators 201. The shaft is in elongated shape. The end effector is provided at the tip of the shaft. The end effector is grasping forceps, scissors, a hook, a high-frequency knife, a snare wire, a clamp, or a stapler, for example. The end effector is not limited to those and can be various types of treatment tools. In surgeries using the patient-side apparatus 200, the three manipulators 201 introduce the surgical instruments 201a to 201c into the body of the patient P through a cannula (trocar) placed on the body surface of the patient P. The end effector of each of the surgical instruments 201a to 201c is then located near the surgery site. The surgical instrument 201a, the surgical instrument 201b, and the surgical instrument 201c are examples of a first surgical instrument, a second surgical instrument, and a replacement surgical instrument of Claims, respectively.

To the tip of one of the four manipulators 201, the endoscope 201d as the medical equipment is detachably attached. The endoscope 201d captures an image within the body cavity of the patient P. The captured image is outputted to the remote control apparatus 100. The endoscope 201d is a 3D endoscope capable of capturing a three-dimensional image or a 2D endoscope. In surgeries using the patient-side apparatus 200, the one of the manipulators 201 introduces the endoscope 201d into the body of the patient P through a trocar placed on the body surface of the patient P. The endoscope 201d is then located near the surgery site.

The remote control apparatus 100 constitutes the interface with the operator O. The remote control apparatus 100 is an apparatus that allows the operator O to operate the medical equipment held by the manipulators 201. Specifically, the remote control apparatus 100 is configured to transmit action mode instructions which are inputted by the operator O and are to be executed by the surgical instruments 201a to 201c and endoscope 201d, to the patient-side apparatus 200 through the controller 206. The remote control apparatus 100 is installed beside the operation table 300 so that the operator O can see the state of the patient P very well while operating operation handles 1 of the remote control apparatus 100, for example. The remote control apparatus 100 may be configured to transmit the action mode instructions wirelessly and installed in a room different from the operation room where the operation table 300 is installed.

The action modes to be executed by the surgical instruments 201a to 201c include a mode of actions to be taken by each of the surgical instruments 201a to 201c (a series of positions and postures) and actions to be executed by the function of each of the surgical instruments 201a to 201c. For one of the surgical instruments 201a to 201c which is a pair of grasping forceps, for example, the action mode to be executed by the surgical instruments 201a to 201c includes roll and pitch positions of the wrist of the end effector and the action to open or close the jaws. For one of the surgical instruments 201a to 201c which is a high-frequency knife, the action mode to be executed by the surgical instruments 201a to 201c includes vibration of the high-frequency knife, specifically, supply of current to the high-frequency knife. For one of the surgical instruments 201a to 201c which is a snare wire, the action mode to be executed by the surgical instruments 201a to 201c includes a capturing action and an action to release the captured object and moreover includes an action to supply current to a bipolar or monopolar instrument to burn off the surgery site.

The action mode to be executed by the endoscope 201d includes setting of the position and posture of the tip of the endoscope 201d or setting of the zoom magnification, for example.

Figure 2:
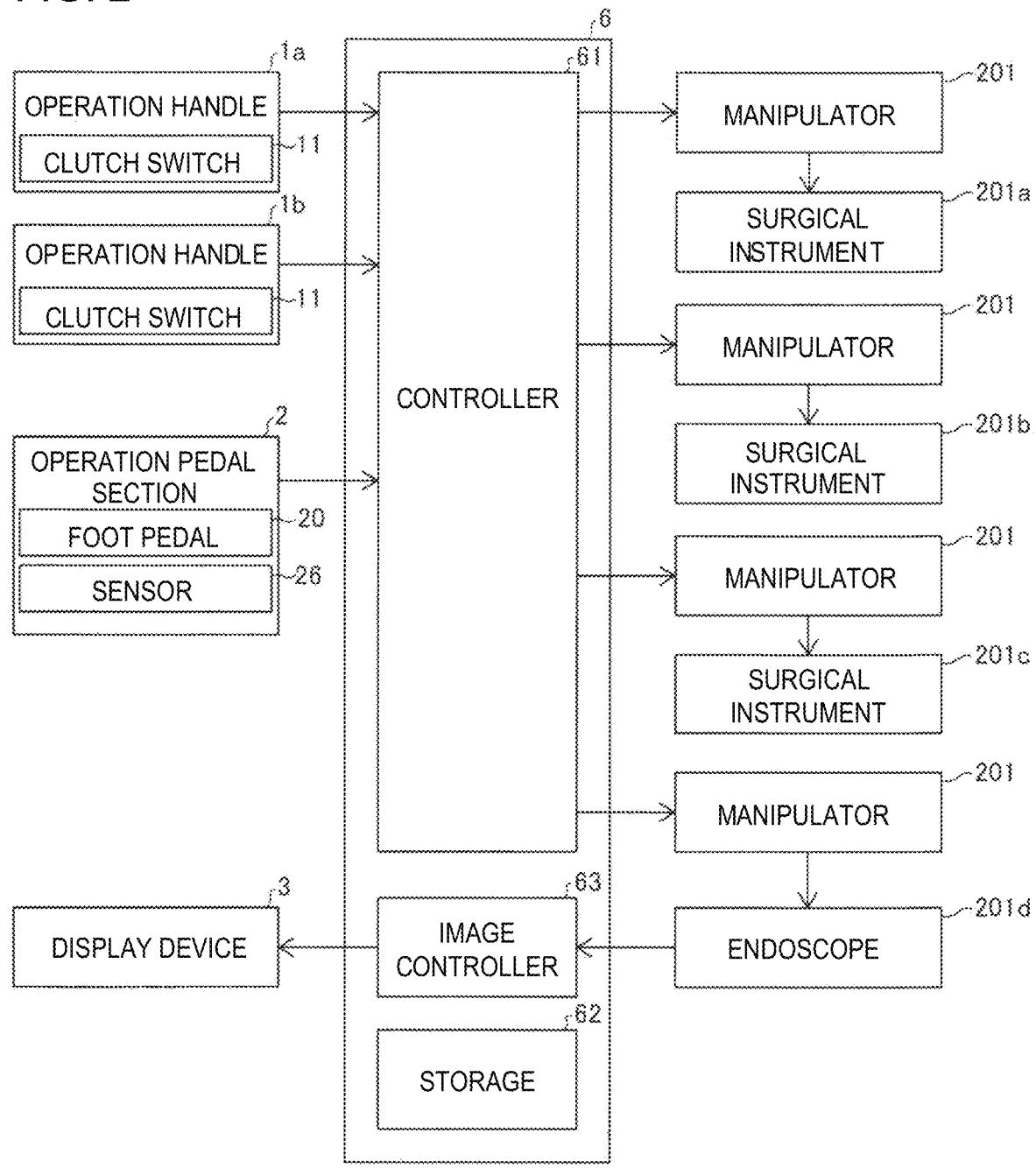
FIG. 2 is a block diagram illustrating a view of a control-related configuration of the surgical system according to an embodiment.

As illustrated in FIGS. 1 and 2, the remote control apparatus 100 includes operation handles 1, an operation pedal section 2, a display device 3, a display device supporting arm 4 supporting the display device 3, an armrest 5 supporting the arms of the operator O, and a control apparatus 6.

The operation handles 1 are provided in order to remotely operate the medical equipment held by the manipulators 201. Specifically, the operation handles 1 accept operations by the operator O for operating the medical equipment (the surgical instruments 201a to 201c and the endoscope 201d). The operation handles 1 include a pair of operation handles 1 arranged side by side in the X direction. The operation handles 1 includes an operation handle 1a, which is arranged on the right side (the X2 side) to be operated by the right hand of the operator O, and an operation handle 1b, which is arranged on the left side (the X1 side) to be operated by the left hand of the operator O. The operation handle 1a and the operation handle 1b are examples of a first operation handle and a second operation handle of Claims, respectively.

The operation handles 1 are arranged to extend from the rear side (the Y2 side) of the remote control apparatus 100 to the front side (the Y1 side) thereof. The operation handles 1 are configured to be movable within a predetermined three-dimensional operation region. Specifically, the operation handles 1 are configured to be movable in the up-down direction (the Z direction), the right-left direction (the X direction), and the front-rear direction (the Y direction).

The right hand-operation handle 1a is provided to remotely operate the corresponding surgical instrument 201a. The left hand-operation handle 1b is provided to remotely operate the corresponding surgical instrument 201b. As illustrated in FIG. 2, a clutch switch 11 is provided in each of the operation handles 1a and 1b. The clutch switch 11 is operated when temporarily disconnecting the control-related connections between the manipulators 201 and the operation handles 1a and 1b. When the clutch switch 11 of the operation handle 1a is operated, the control-related connection between the operation handle 1a and one of the manipulators 201 to which the surgical instrument 201a is provided is temporarily disconnected. When the clutch switch 11 of the operation handle 1b is operated, the control-related connection between the operation handle 1b and another one of the manipulators 201 to which the surgical instrument 201b is provided is temporarily disconnected.

The remote control apparatus 100 and patient-side apparatus 200 constitute a master-slave system in terms of controlling motion of the manipulators 201. Specifically, the operation handles 1 constitute an operating section on the master side in the master-slave system, and the manipulators 201 supporting the medical equipment constitute an operating section on the slave side. When the operator O operates the operation handles 1, the motion of the manipulators 201 is controlled so that the tips (the end effectors of the surgical instruments 201a to 201c or the endoscope 201d) of the manipulators 201 move following the movement of the operation handles 1.

The patient-side apparatus 200 is configured to control the motion of the manipulators 201 in accordance with the set motion scaling ratio. When the motion scaling ratio is set to ½, for example, the end effectors of the surgical instruments 201a to 201c move ½ of the movement distance of the operation handles 1. This allows for precise fine surgery.

Figure 3:
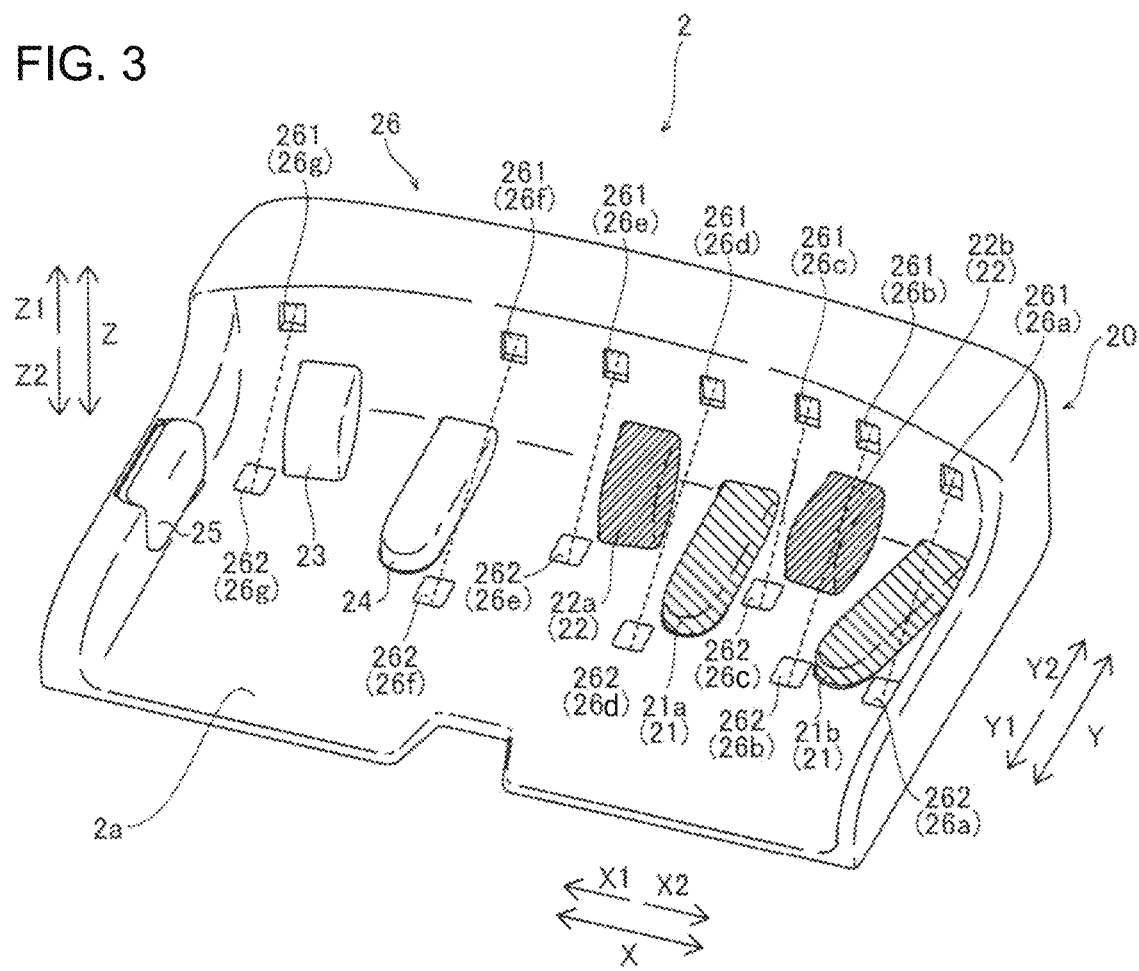
FIG. 3 is a diagram illustrating a perspective view of an operation pedal section of a remote control apparatus according to an embodiment.
Figure 4:
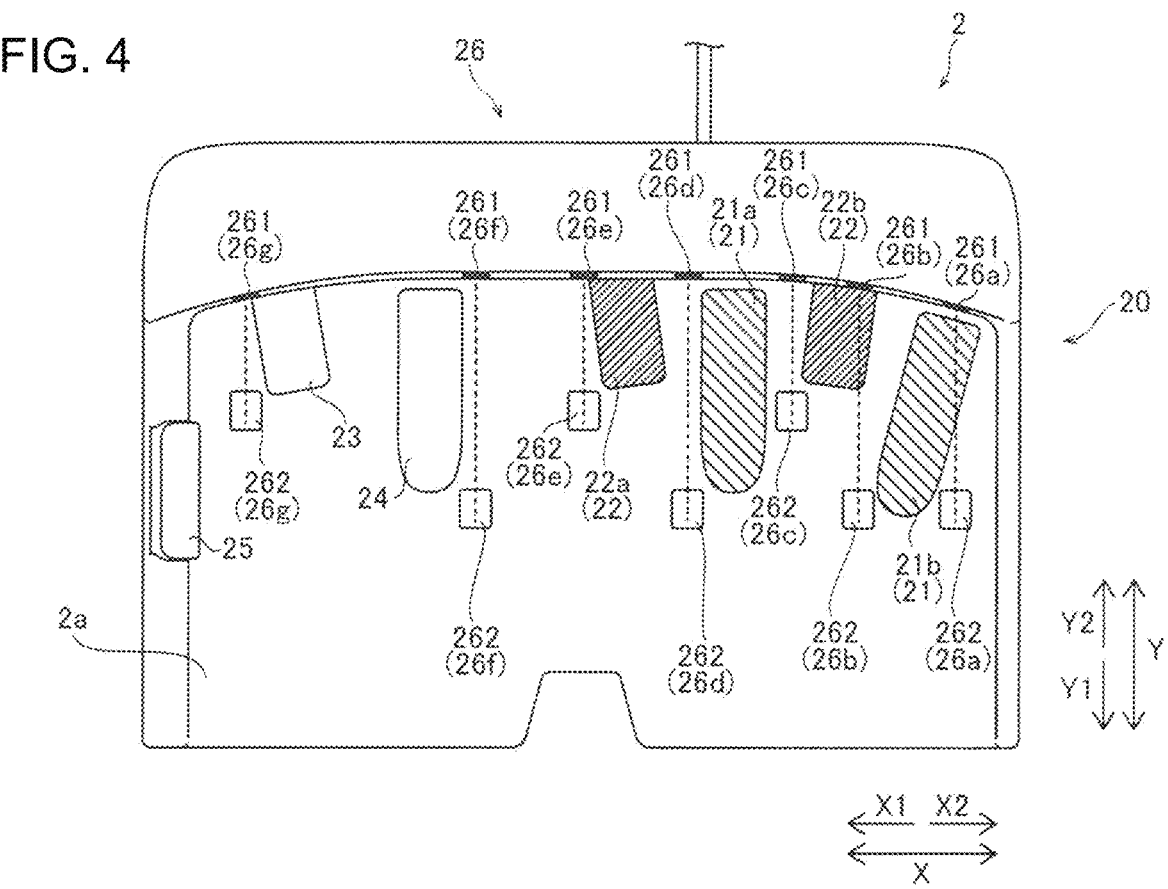
FIG. 4 is a diagram illustrating a plan view of the operation pedal section of the remote control apparatus according to an embodiment.
Figure 5:
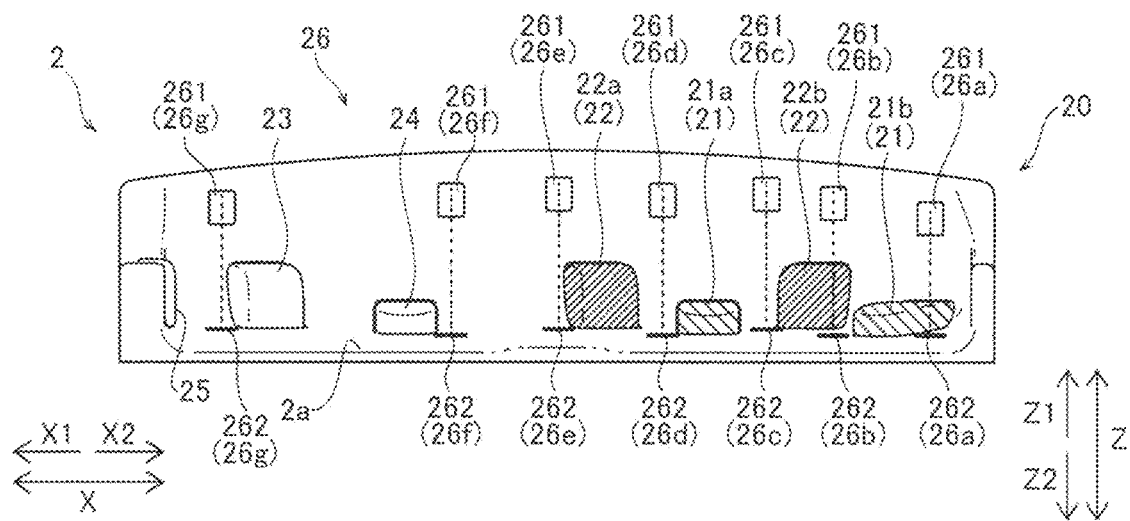
FIG. 5 is a diagram illustrating a front view of the operation pedal section of the remote control apparatus according to an embodiment.

As illustrated in FIGS. 3 to 5, the operation pedal section 2 includes foot pedals 20 that execute functions of the medical equipment. The foot pedals 20 are arranged on a base 2a. The foot pedals 20 include coagulation pedals 21, cutting pedals 22, a clutch pedal 23, and a camera pedal 24. Additionally, the operation pedal section 2 is provided with a switch pedal 25. The coagulation pedals 21, cutting pedals 22, clutch pedal 23, and camera pedal 24 are operated by being pressed downward. The switch pedal 25 is operated by being pressed in the horizontal direction. The foot pedals 20 are operated by the foot of the operator O.

The operation pedal section 2 includes sensors 26 that detect the presence of the foot operating the foot pedals 20. The sensors 26 include sensors 26a, 26b, 26c, 26d, 26e, 26f, and 26g. The sensors 26 each include an emitter 261 and a receiver 262. The sensors 26 detect the presence of the foot when the light from the emitter 261 is blocked by the foot and the light reception by the receiver 262 is interrupted. Specifically, the sensors 26 are blockage type sensors. The sensors 26 are provided to detect that the foot of the operator O is put on any one of the foot pedals 20. In other words, the sensors 26 detect setting of the foot of the operator O at an operation preparation position of the foot pedal 20.

The detection information detected by the sensors 26 is transmitted to a controller 61, and the controller 61 that receives the detection information determines whether there is the foot operating the corresponding foot pedals 20.

The coagulation pedals 21 enable surgical instruments to coagulate surgery sites. Specifically, when the coagulation pedals 21 are operated, voltage for coagulation is applied to corresponding one of the surgical instruments 201a, 201b and 201c to coagulate surgery sites. The coagulation pedals 21 include a coagulation pedal 21a and a coagulation pedal 21b. The coagulation pedal 21a is located to the left (on the X1 side) of the coagulation pedal 21b. The coagulation pedal 21a is used in relation to the surgical instrument 201b controlled by the left hand-operation handle 1b. The coagulation pedal 21b is used in relation to the surgical instrument 201a controlled by the right hand-operation handle 1a. The coagulation pedals 21a and 21b are in a first color. For example, the coagulation pedals 21a and 21b are in blue as the first color.

The cutting pedals 22 enable the surgical instruments to cut surgery sites. Specifically, when the cutting pedals 22 are operated, voltage for cutting is applied to corresponding one of the surgical instruments 201a, 201b, and 201c to cut surgery sites. The cutting pedals 22 include a cutting pedal 22a and a cutting pedal 22b. The cutting pedal 22a is located to the left (on the X1 side) of the cutting pedal 22b. The cutting pedal 22a is used in relation to the surgical instrument 201b controlled by the left hand-operation handle 1b. The cutting pedal 22b is used in relation to the surgical instrument 201a controlled by the right hand-operation handle 1a. The cutting pedals 22a and 22b are in a second color different from the first color. For example, the cutting pedals 22a and 22b are in yellow as the second color.

Specifically, the right-side foot pedals (the coagulation pedal 21b and the cutting pedal 22b) execute the function of the surgical instrument 201a operated by the right hand-operation handle 1a. The left-side foot pedals (the coagulation pedal 21a and the cutting pedal 22a) execute the function of the surgical instrument 201b operated by the left hand-operation handle 1b. The coagulation pedal 21b is an example of a first foot pedal and a first coagulation pedal of Claims, and the cutting pedal 22b is an example of the first foot pedal and a first cutting pedal of Claims. The coagulation pedal 21a is an example of a second foot pedal and a second coagulation pedal of Claims, and the cutting pedal 22a is an example of the second foot pedal and a second cutting pedal of Claims.

The clutch pedal 23 is operated to execute a clutch function. Specifically, the clutch pedal 23 is used when temporarily disconnecting the control-related connections between the manipulators 201 and the operation handles 1a and 1b to stop the operation of the surgical instruments. During the operation of the clutch pedal 23, the manipulators 201 of the patient-side apparatus 200 does not move even when the operation handles 1a and 1b are operated. For example, when the operation handles 1 come close to the end of the movable region during the operation, it is possible to move the operation handles 1 back to near the central position by operating the clutch pedal 23 and temporarily disconnecting the control-related connections. Then, once the operation of the clutch pedal 23 is quitted, the manipulators 201 and the operation handles 1 are connected again, and operation of the operation handles 1 can be restarted from near the central position. In this case, the clutch pedal 23 is operated to temporarily disconnect the whole control-related connections between both the operation handles 1a and 1b and the manipulators 201. On the other hand, the clutch switch 11 provided in each of the operation handles 1a and 1b is operated to temporarily disconnect the control-related connections between either of the operation handles 1a and 1b and corresponding one of the manipulators 201, individually. The clutch pedal 23 is an example of a fifth foot pedal of Claims.

The camera pedal 24 is used to control the position and orientation of the endoscope 201d that captures images within the body cavity. That is, the camera pedal 24 executes a function of the endoscope 201d. Specifically, the camera pedal 24 enables control of the endoscope 201d by the operation handles 1. That is, the position and orientation of the endoscope 201d are controllable by the operation handles 1 while the camera pedal 24 is being pressed. The endoscope 201d is controlled by using both of the right and left operation handles 1, for example. Specifically, when the operator O rotates the right and left operation handles 1 about the middle point between the right and left operation handles 1, the endoscope 201d is rotated. When the operator O presses the right and left operation handles 1 together, the endoscope 201d goes further into the body cavity. When the operator O pulls the right and left operation handles 1 together, the endoscope 201d retracts. When the operator O moves the right and left operation handles 1 together up, down, right, and left, the endoscope 201d moves up, down, right, and left, respectively. The camera pedal 24 is an example of a third foot pedal of Claims.

The switch pedal 25 is used to switch the manipulators 201 to be operated by the operation handles 1. For example, four manipulators 201 are provided, and within three of the manipulators 201 respectively holding the surgical instruments 201a to 201c, the manipulators 201 operated by the right and left operation handles 1 are switched by operating the switch pedal 25. Specifically, the switch pedal 25 is operated to replace the surgical instrument 201a operated by the right hand-operation handle 1a or the surgical instrument 201b operated by the left hand-operation handle 1b with the surgical instrument 201c, which is provided for replacement.

The switch pedal 25 is operated by being pressed leftward (in the X1 direction). For example, the manipulator 201 operated by the right hand-operation handle 1*a* is switched by operating the switch pedal 25. In this case, the manipulator 201 operated by the right hand-operation handle 1*a* is switched without changing the manipulator 201 operated by the left hand-operation handle 1*b*. For example, the manipulator 201 operated by the left hand-operation handle 1*b* is switched by operating the switch pedal 25. In this case, the manipulator 201 operated by the left hand-operation handle 1*b* is switched without changing the manipulator 201 operated by the right hand-operation handle 1*a*. The switch pedal 25 is an example of a fourth foot pedal of Claims.

As illustrated in FIGS. 3 to 5, the foot pedals 20 are arranged from the left side (the X1 side) to the right side (the X2 side) in order of the switch pedal 25, the clutch pedal 23, the camera pedal 24, the cutting pedal 22*a*, the coagulation pedal 21*a*, the cutting pedal 22*b*, and the coagulation pedal 21*a*.

The arrangement of the foot pedals 20 illustrated in FIGS. 3 to 5 is suitable for operating the pairs of coagulation pedals 21 and cutting pedals 22 assigned to the respective right and left operation handles 1 with only the right foot. The pedals arrangement may be as follows: the pair of coagulation pedal 21*a* and cutting pedal 22*a* is located to the left (the X1 side) of the clutch pedal 23 and camera pedal 24, and the clutch pedal 23 and camera pedal 24 are located at the center (between the pair of coagulation pedal 21*a* and cutting pedal 22*a* and the pair of coagulation pedal 21*b* and cutting pedal 22*b*). This arrangement is suitable for operating the coagulation pedal 21*a* and cutting pedal 22*a* assigned to the left hand-operation handle 1*b* with the left foot while operating the coagulation pedal 21*b* and cutting pedal 22*b* assigned to the right hand-operation handle 1*a* with the right foot.

The base 2*a* on which the foot pedals 20 are arranged is movable in the horizontal direction. Specifically, two sides in the axial direction (the X direction) of the base 2*a* are connected with a base of the remote control apparatus 100 with sliding bearings, and the operation pedal section 2 is slidable and movable in the depth direction (the front-rear direction, the Y direction). The operation pedal section 2 can be moved in the depth direction electrically by a driver device such as a motor provided in the base of the remote control apparatus 100. This makes it possible to adjust the positions of the foot pedals 20 depending on the operation posture, physique, or preference of the operator O.

The number of the sensors 26 that detect the presence of the foot is greater than the number of the foot pedals 20 that are operated by being pressed downward. Specifically, the number of the provided sensors 26 is seven. On the other hand, the number of the provided foot pedals 20 operated by being pressed downward is six (the coagulation pedals 21*a* and 21*b*, cutting pedals 22*a* and 22*b*, clutch pedal 23, and camera pedal 24).

The sensors 26 used to detect the foot moved for the operation are provided near one of the foot pedals 20, and the sensors 26 are used to determine whether there is the foot that is operating or that is trying to operate the one of the foot pedals 20. Specifically, when the controller 61 receives the detection information from the sensors 26 located near the one of the foot pedals 20, the controller 61 determines that the foot of the operator O is set at the operation preparation position of the one of the foot pedals 20.

In order to simplify the descriptions, in this specification, a configuration in which one of the sensors 26 (for emitter-receiver type sensors, that is straight light emitted from an emitter) is positioned between a central section of a tip side (the Y1 side) of one foot pedal 20 and a central section of a tip side (the Y1 side) of another foot pedal 20 next to the one foot pedal 20 is expressed simply as "a sensor is positioned between one pedal and another pedal next to the one pedal." In addition, in this specification, the sensor 26 positioned in a central section of a tip side (the Y1 side) of one foot pedal 20 (for the emitter-receiver type sensors, that is a sensor including an emitter that emits straight light passing through the central section of the tip side of the one foot pedal 20) and a sensor between the one pedal and another pedal next to the one pedal are each defined as "a sensor arranged near one pedal."

The sensors 26*a* and 26*b* detect the foot coming closer to the coagulation pedal 21*b*. Specifically, when both the sensors 26*a* and 26*b* detect the foot, the controller 61 determines that the foot pedal 20 to be operated is the coagulation pedal 21*b*. The sensors 26*b* and 26*c* detect the foot coming closer to the cutting pedal 22*b*. Specifically, when both the sensors 26*b* and 26*c* detect the foot, the controller 61 determines that the foot pedal 20 to be operated is the cutting pedal 22*b*.

The sensors 26*c* and 26*d* detect the foot coming closer to the coagulation pedal 21*a*. Specifically, when both the sensors 26*c* and 26*d* detect the foot, the controller 61 determines that the foot pedal 20 to be operated is the coagulation pedal 21*a*. The sensors 26*d* and 26*e* detect the foot coming closer to the cutting pedal 22*a*. Specifically, when both the sensors 26*d* and 26*e* detect the foot, the controller 61 determines that the foot pedal 20 to be operated is the cutting pedal 22*a*.

The sensor 26*f* detects the foot coming closer to the camera pedal 24. Specifically, when the sensor 26*f* detects the foot, the controller 61 determines that the foot pedal 20 to be operated is the camera pedal 24. The sensor 26*g* detects the foot coming closer to the clutch pedal 23. Specifically, when the sensor 26*g* detects the foot, the controller 61 determines that the foot pedal 20 to be operated is the clutch pedal 23.

The emitter 261 includes a light-emitting element such as an LED. The emitter 261 is configured to emit visible light or invisible light such as infrared light. The receiver 262 includes a light-receiving element. The corresponding emitter 261 and receiver 262 are arranged along the Y direction in the plan view. Specifically, as illustrated as a broken line in FIGS. 3 and 5, the light from the emitter 261 is emitted substantially along the Y direction in the plan view. The corresponding emitter 261 and receiver 262 are arranged so that their arrangement orientation is parallel to each other in the plan view. The emitter 261 is configured to emit the light obliquely downward.

An assignment example of the coagulation pedals 21 (21*a* and 21*b*) and the cutting pedals 22 (22*a* and 22*b*) on the operation pedal section 2 is described with reference to FIG. 6. The coagulation pedal 21*a* and the cutting pedal 22*a* are used as a pair, while the coagulation pedal 21*b* and the cutting pedal 22*b* are used as a pair. In this case, it is possible to use a pair of forceps (e.g., a grasper) to cut and coagulate the surgery site. When a pair of forceps is used for cutting and coagulating, high voltage is applied for cutting, and voltage lower than the cutting case is applied for coagulating. Specifically, it is possible to coagulate and cut the surgery site by selecting and using the coagulation pedal 21*a* (21*b*) and the cutting pedal 22*a* (22*b*). Although a grasper and the like can be used for cutting and coagulating, a sealing device for coagulating may also be used as a dedicated tool or used concurrently with another tool. This is because the sealing device often has an additional function such as automatic termination of power supply that is executed when coagulating is completed.

Figure 6:
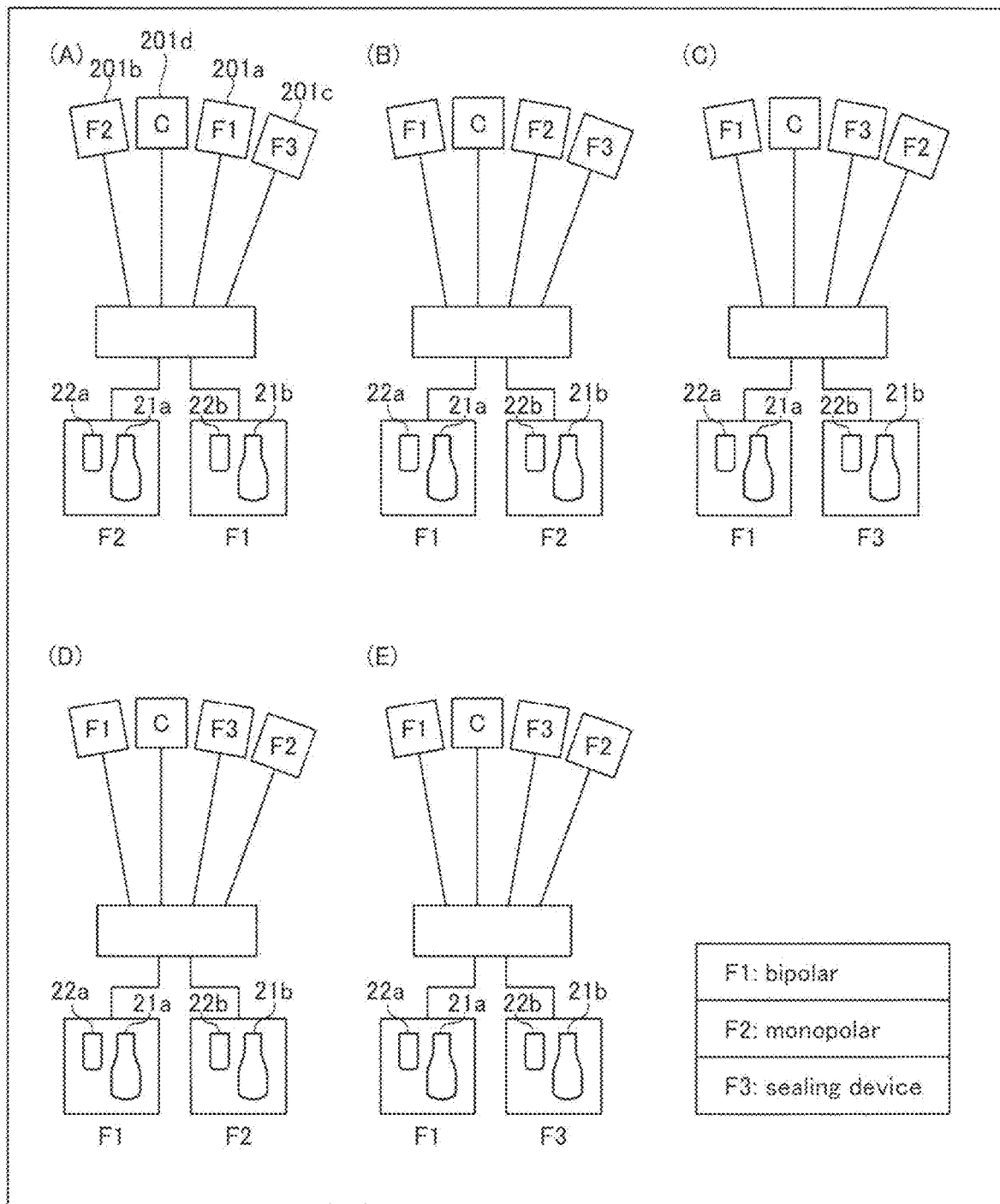
FIG. 6 is a diagram illustrating views for explaining assignment examples of the operation pedal section of the remote control apparatus according to an embodiment.

In the example illustrated in FIG. 6, a pair of bipolar forceps F1, a pair of monopolar forceps F2, and a sealing device F3 as the medical equipment and the endoscope 201d are attached to the four manipulators 201. The positional relationship between the four manipulators 201 is recognized by the position detector provided for each manipulator. The positional relationship between the manipulators in the right-left direction is determined based on the positions thereof seen from the platform 203. In FIG. 6A, the pair of monopolar forceps F2 is located to the left of one of the manipulators 201 to which the endoscope 201d is attached, and the pair of bipolar forceps F1 and the sealing device F3 are located to the right of the manipulator 201 to which the endoscope 201d is attached in this order from left. In the assignment of the coagulation pedals 21 (21a and 21b) and cutting pedals 22 (22a and 22b), the manipulator 201 to which the surgical instrument 201b is attached is assigned to the left-side foot pedals (the coagulation pedal 21a and the cutting pedal 22a), and the manipulator 201 to which the surgical instrument 201a, which is a surgical instrument to the right of the manipulator 201 to which the surgical instrument 201b is attached, is assigned to right-side foot pedals (the coagulation pedal 21b and cutting pedal 22b). Specifically, in FIG. 6A, the pair of monopolar forceps F2 is assigned to the left-side foot pedals (the coagulation pedal 21a and the cutting pedal 22a), while the pair of bipolar forceps F1 is assigned to the right-side foot pedals (the coagulation pedal 21b and the cutting pedal 22b). When only two surgical instruments are attached, the manipulators 201 are assigned to the left-side foot pedals and the right-side foot pedals in order from the one on the leftmost side of the manipulator 201 to which the endoscope 201d is attached. When only one surgical instrument is attached, the manipulator 201 is assigned to the left-side foot pedals.

In FIG. 6B, the pair of bipolar forceps F1 and the pair of monopolar forceps F2 are replaced with each other by an assistant (a nurse, for example). In this case, the types of the surgical instruments 201a and 201b are specified when the surgical instruments 201a and 201b are attached to the manipulators 201. For example, the IC of the interface may store information including model numbers of the instruments. The pair of bipolar forceps F1 is assigned to the left-side foot pedals (the coagulation pedal 21a and the cutting pedal 22a). The pair of monopolar forceps F2 is assigned to the right-side foot pedals (the coagulation pedal 21b and the cutting pedal 22b).

In FIG. 6C, the pair of monopolar forceps F2 and the sealing device F3 are replaced with each other by an assistant (a nurse, for example). In this case, the types of the surgical instruments 201a and 201b are specified when the surgical instruments 201a and 201b are attached to the manipulators 201. The pair of bipolar forceps F1 continues to be assigned to the left-side foot pedals (the coagulation pedal 21a and the cutting pedal 22a). The sealing device F3 is assigned to the right-side foot pedals (the coagulation pedal 21b and the cutting pedal 22b).

In FIG. 6D, the switch pedal 25 is operated to change which of the two manipulators 201 located on the right side is being activated. Specifically, the manipulators 201 controlled by the operation handles 1 are switched. The manipulator 201 to which the pair of bipolar forceps F1 is attached is controlled with the left hand-operation handle 1b while the manipulator 201 to which the pair of monopolar forceps F2 is attached is controlled with the right hand-operation handle 1a. The pair of bipolar forceps F1 continues to be assigned to the left-side foot pedals (the coagulation pedal 21a and the cutting pedal 22a). The pair of monopolar forceps F2 is assigned to the right-side foot pedals (the coagulation pedal 21b and the cutting pedal 22b).

In FIG. 6E, the switch pedal 25 is operated to change which of the two manipulators 201 on the right side is being activated. Specifically, the manipulators 201 to be controlled by the operation handles 1 are switched. The manipulator 201 to which the pair of bipolar forceps F1 is attached is controlled with the left hand-operation handle 1b while the manipulator 201 to which the sealing device F3 is attached is controlled with the right hand-operation handle 1a. The pair of bipolar forceps F1 continues to be assigned to the left-side foot pedals (the coagulation pedal 21a and the cutting pedal 22a). The sealing device F3 is assigned to the right-side foot pedals (the coagulation pedal 21b and the cutting pedal 22b).

In some cases, a simple grasper which works without electricity is used when strong grip is mainly necessary. Such surgical instruments that cannot be supplied with current are not controlled with the coagulation pedals 21 (21a and 21b) and the cutting pedals 22 (22a and 22b) and are therefore not assigned to the coagulation pedals 21 and cutting pedals 22. The assignment of the coagulation pedals 21 (21a and 21b) and cutting pedals 22 (22a and 22b) is configured so that the manipulator 201 holding a surgical instrument that cannot be supplied with current is ignored.

The left-side foot pedals (the coagulation pedal 21a and the cutting pedal 22a) and right-side foot pedals (the coagulation pedal 21b and the cutting pedal 22b) may be assigned by another rule. For example, the manipulators 201 to the right and left of the manipulator 201 to which the endoscope 201d is attached may be always assigned to the foot pedals. For example, the one manipulator 201 to the left of the manipulator 201 to which the endoscope 201d is attached may be assigned to the left-side foot pedals (the coagulation pedal 21a and the cutting pedal 22a), while the left manipulator 201 among the two manipulators 201 located to the right of the manipulator 201 to which the endoscope 201d is attached is assigned to the right-side foot pedals (the coagulation pedal 21b and the cutting pedal 22b).

As illustrated in FIG. 1, the display device 3 displays an image captured by the endoscope 201d. The display device 3 includes a scope type display device or a non-scope type display device. In the example illustrated in FIG. 1, the display device 3 is the scope type display device. The scope type display device is a display unit that the operator O looks into, for example. The non-scope type display device is a concept including an open-type display unit that the operator O looks at without looking into and that has a flat screen, such as a normal personal computer display.

As illustrated in FIG. 2, the control apparatus 6 such as a computer includes a controller 61, a storage 62, and an image controller 63, for example. The controller 61 includes a computing element such as a CPU. The storage 62 includes one or more memories, such as a ROM and a RAM. The control apparatus 6 is configured to control at least the display device 3. The control apparatus 6 may be composed of a single controller performing centralized control or may be composed of plural controllers that perform decentralized control in cooperation with each other. The controller 61 determines whether the action mode instruction inputted by the operation handles 1 is to be executed by the surgical instruments 201a to 201c or to be executed by the endoscope 201d, depending on the state of the operation pedal section 2. The controller 61 transmits a signal to operate a corresponding one of the manipulators 201 based on the determination result and operations through the operation handles 1.

The controller 61 receives the detection information on the presence of the foot of the operator O from the sensors 26 and determines whether there is the foot of the operator O. When it is determined that there is the foot of the operator O, the controller 61 controls the display device 3 to display the corresponding screen.

The storage 62 stores control programs corresponding to the types of the surgical instruments 201a to 201c, for example. The controller 61 reads the stored control programs according to the types of the attached surgical instruments 201a to 201c. The action mode instructions from the operation handles 1 and/or the operation pedal section 2 of the remote control apparatus 100 thereby causes the respective surgical instruments 201a to 201c to perform proper motions.

The image controller 63 transmits an image acquired by the endoscope 201d to the display device 3. The image controller 63 modifies the image if necessary.

Figure 7:
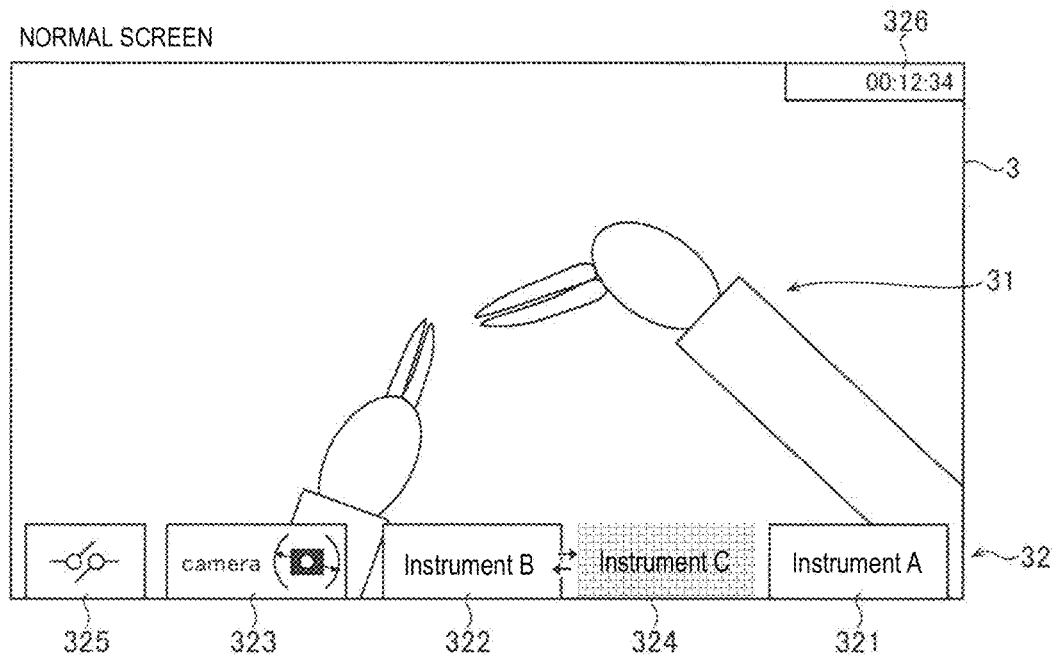
FIG. 7 is a diagram illustrating a view of an example of a normal screen displayed on a display device according to an embodiment.

As illustrated in FIG. 7, in an embodiment, the control apparatus 6 is configured to display a graphical user interface 32 on the display device 3 while overlapping the graphical user interface 32 on an image 31 captured by the endoscope 201d. The graphical user interface 32 includes a first area 321 showing information on the surgical instrument 201a operated by the right hand-operation handle 1a, a second area 322 showing information on the surgical instrument 201b operated by the left hand-operation handle 1b, and a third area 323 showing information on the endoscope 201d, which are arranged side by side in this order from right to left. It is possible to display the first area 321, the second area 322, and the third area 323, which respectively show the information on the surgical instrument 201a, the surgical instrument 201b, and the endoscope 201d respectively supported by the manipulators 201, to be arranged side by side on the same level. Consequently, the operator O does not need to move the eyes a lot to check the pieces of information on the surgical instrument 201a, the surgical instrument 201b, and the endoscope 201d respectively supported by the manipulators 201. As a result, it is possible to suppress degradation of the visibility of the information on the surgical instruments 201a and 201b, and the endoscope 201d supported by the manipulators 201.

In an embodiment, the control apparatus 6 is configured to display the graphical user interface 32 on the display device 3 while overlapping the graphical user interface 32 on the image 31 captured by the endoscope 201d. The graphical user interface 32 includes the first area 321 showing the information on the surgical instrument 201a operated by the right hand-operation handle 1a, the second area 322 showing the information on the surgical instrument 201b operated by the left hand-operation handle 1b, and the third area 323 showing the information on the endoscope 201d. The first area 321, second area 322, and third area 323 are arranged in the same order as the arrangement order of the right-side foot pedals (the coagulation pedal 21b and the cutting pedal 22b), left-side foot pedals (the coagulation pedal 21a and the cutting pedal 22a), and camera pedal 24 on the operation pedal section 2. The arrangement order of the displayed information on the surgical instrument 201a, surgical instrument 201b, and endoscope 201d coincides with the arrangement order of the corresponding foot pedals 20. Thus, the operator O can instinctively grasp the positions of the foot pedals 20 based on the positions of the displayed information on the surgical instrument 201a, surgical instrument 201b, and endoscope 201d.

As illustrated in FIG. 7, the graphical user interface 32 displayed on the display device 3 includes the first area 321, the second area 322, the third area 323, a fourth area 324, and a fifth area 325. Additionally, the graphical user interface 32 includes a status area 326. Moreover, the graphical user interface 32 includes a pop-up area 327a (see FIG. 9), a pop-up area 327b (see FIG. 13), a pop-up area 327c (see FIG. 15), and a pop-up area 327d (see FIG. 17). Furthermore, the graphical user interface 32 includes a central area in which a level 328 (see FIG. 14) for the endoscope 201d is displayed. The graphical user interface 32 also includes an error notification area 329a (see FIG. 20) and an error notification area 329b (see FIG. 21).

The first area 321, second area 322, third area 323, fourth area 324, and fifth area 325 of the graphical user interface 32 are arranged side by side in a lower end region of the display device 3. The first area 321, second area 322, third area 323, fourth area 324, and fifth area 325 of the graphical user interface 32 may be arranged side by side in an upper end region of the display device 3. The pieces of information on the surgical instrument 201a, surgical instrument 201b, and endoscope 201d are displayed on the upper side or the lower side of the display device 3. Unlike the case where the pieces of information are displayed in the center region of the display device 3 other than the lower and upper end regions, it is possible to prevent the difficulty in viewing of the image 31 captured by the endoscope 201d caused by the first area 321, second area 322, third area 323, fourth area 324, and fifth area 325.

The pop-up areas 327a and 327b of the graphical user interface 32 are arranged on the left side in the right-left direction and near the center in the up-down direction of the display device 3. The pop-up areas 327c and 327d of the graphical user interface 32 are arranged on the right side in the right-left direction and near the center in the up-down direction of the display device 3. The status area 326 and the error notification area 329a of the graphical user interface 32 are arranged in the upper end region of the display device 3. The error notification area 329b is arranged above the second area 322 of the graphical user interface 32.

The first area 321 displays the type of the surgical instrument 201a being operated by the right-hand operation handle 1a. The second area 322 displays the type of the surgical instrument 201b being operated by the left-hand operation handle 1b. The third area 323 displays the information on the endoscope 201d. Thus, the operator O can easily grasp the types of the surgical instrument 201a being operated by the operation handle 1a and surgical instrument 201b being operated by the operation handle 1b. Additionally, the operator O can easily grasp the state of the endoscope 201d based on the information representing the endoscope 201d.

The fourth area 324 is arranged between the first area 321 and the second area 322. The fourth area 324 displays the information on the replacement surgical instrument 201c. Specifically, the fourth area 324 displays the type of the replacement surgical instrument 201c. Thus, the operator O can easily grasp the information on the replacement surgical instrument 201c, which is to be replaced with the surgical instrument 201a or the surgical instrument 201b and operated by the operation handle 1a or the operation handle 1b. The information in the fourth area 324 is displayed with paler color than the information in the first area 321 and second area 322. In other words, the information in the fourth area 324 is displayed to be more inconspicuous than the information in the first area 321 and second area 322.

The fifth area 325 is arranged to the left of the second area 322. The fifth area 325 displays the information on the clutch function. Specifically, the fifth area 325 displays the operation state of the clutch pedal 23. Thus, the fifth area 325 can display the state of the clutch pedal 23, which is used when temporarily disconnecting the control-related connections between the manipulators 201 and the operation handles 1 and stopping the operations of the surgical instruments 201a and 201b.

The status area 326 displays the status of the surgical system 400. For example, the status area 326 displays duration of surgery procedure. The status area 326 also displays brightness adjustment information and contrast adjustment information of the display device 3.

The pop-up areas 327a to 327d are arranged in positions different from those of the first area 321, second area 322, and third area 323. The pop-up areas 327a to 327d display information, based on a fact that at least one of the sensors 26 detects setting of the foot of the operator O at the operation preparation position of the corresponding foot pedal 20.

Figure 9:
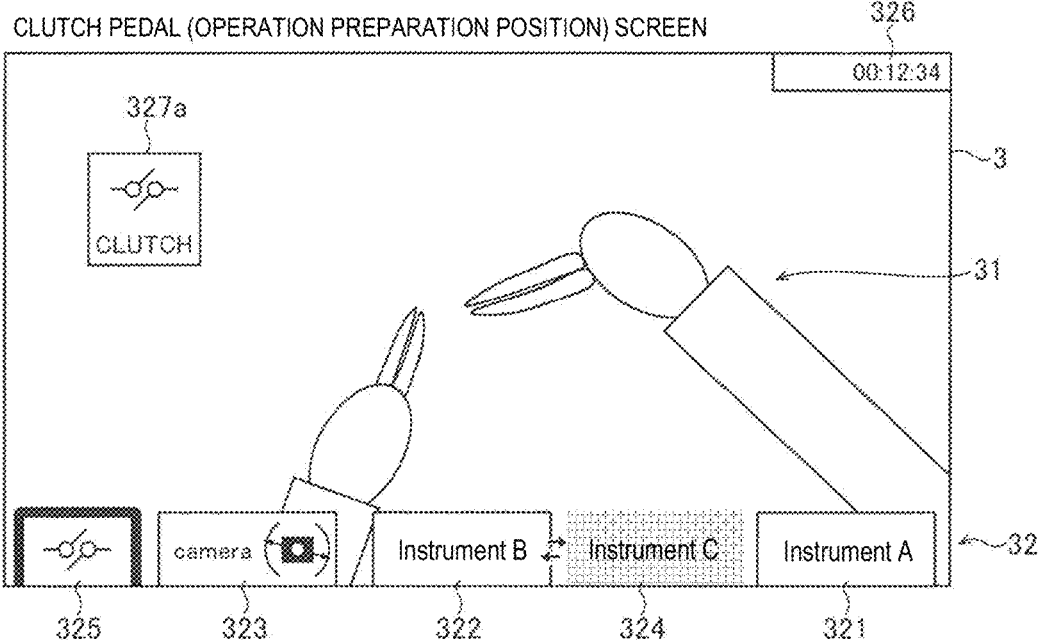
FIG. 9 is a diagram illustrating a view of an example of a screen of the display device when a foot is at an operation preparation position for a clutch pedal according to an embodiment.

As illustrated in FIG. 9, the pop-up area 327a displays the information on the clutch pedal 23 when the foot of the operator O is set at the operation preparation position of the clutch pedal 23. The pop-up area 327a displays information for a predetermined time (e.g., three seconds). Specifically, the display of the information in the pop-up area 327a ends when the foot of the operator O is moved from the operation preparation position of the clutch pedal 23, when the clutch pedal 23 is operated, or after a lapse of the predetermined time.

Figure 13:
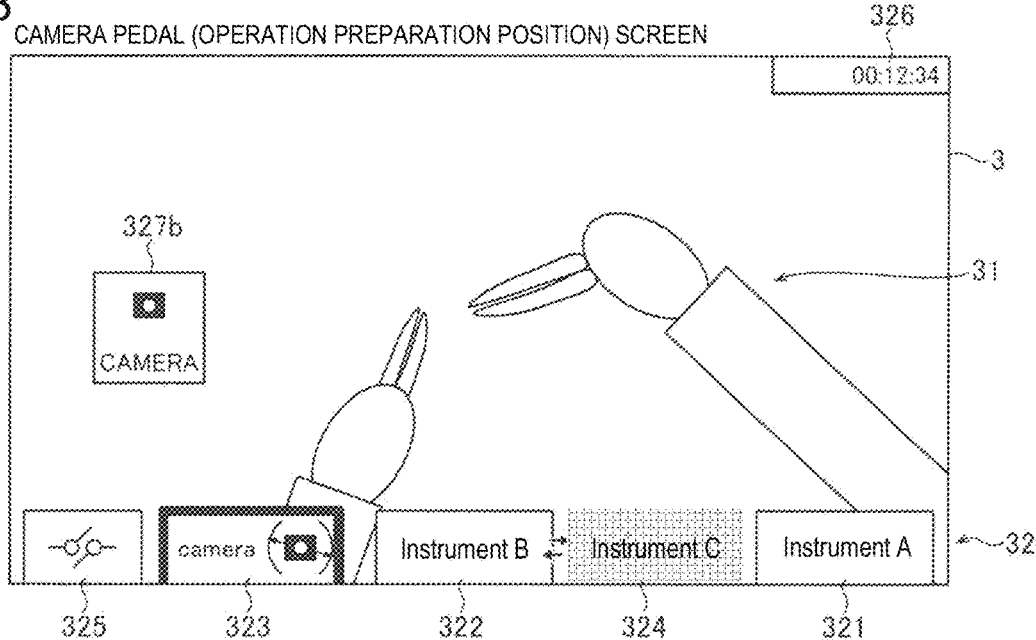
FIG. 13 is a diagram illustrating a view of an example of a screen of the display device when a foot is at an operation preparation position for a camera pedal according to an embodiment.

As illustrated in FIG. 13, the pop-up area 327b displays information on the camera pedal 24 when the foot of the operator O is set at the operation preparation position of the camera pedal 24. The pop-up area 327b displays information for a predetermined time (e.g., three seconds). Specifically, the display of the information in the pop-up area 327b ends when the foot of the operator O is moved from the operation preparation position of the camera pedal 24, when the camera pedal 24 is operated, or after a lapse of the predetermined time.

As illustrated in FIG. 15, the pop-up area 327c displays information on the cutting pedals 22 when the foot of the operator O is set at the operation preparation position of the cutting pedal 22a or 22b. The pop-up area 327c displays information for a predetermined time (e.g., three seconds). Specifically, the display of the information in the pop-up area 327c ends when the foot of the operator O is moved from the operation preparation position of the cutting pedal 22a or 22b, when the cutting pedal 22a or 22b is operated, or after a lapse of the predetermined time.

Figure 17:
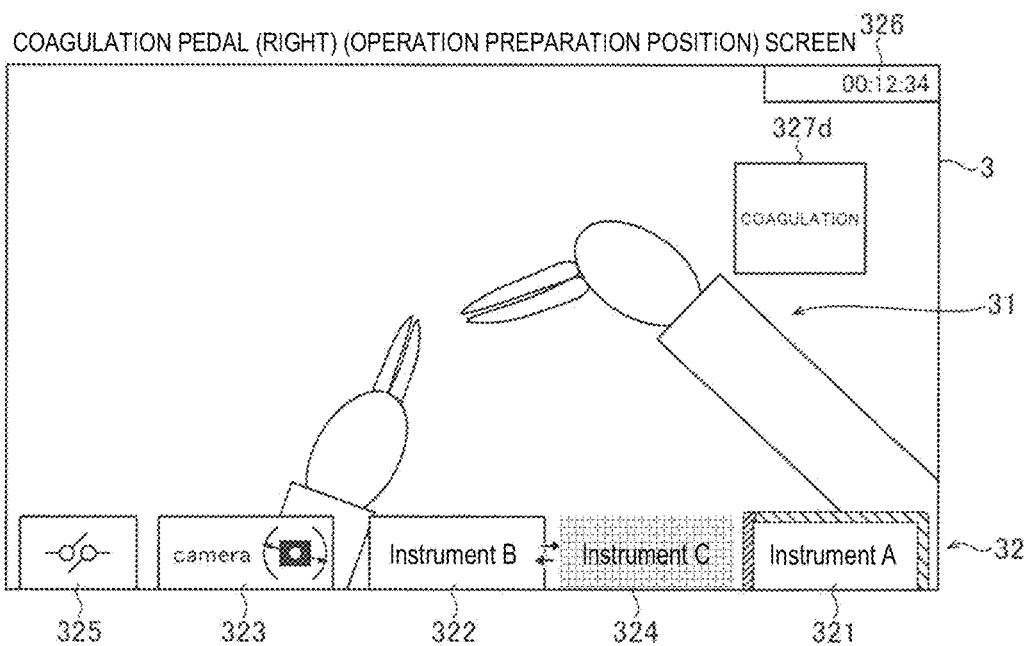
FIG. 17 is a diagram illustrating a view of an example of a screen of the display device when a foot is at an operation preparation position for a coagulation pedal (right) according to an embodiment.

As illustrated in FIG. 17, the pop-up area 327d displays information on the coagulation pedals 21 when the foot of the operator O is set at the operation preparation position of the coagulation pedal 21a or 21b. The pop-up area 327d displays information for a predetermined time (e.g., three seconds). Specifically, the display of the information in the pop-up area 327d ends when the foot of the operator O is moved from the operation preparation position of the coagulation pedal 21a or 21b, when the coagulation pedal 21a or 21b is operated, or after a lapse of the predetermined time.

Figure 14:
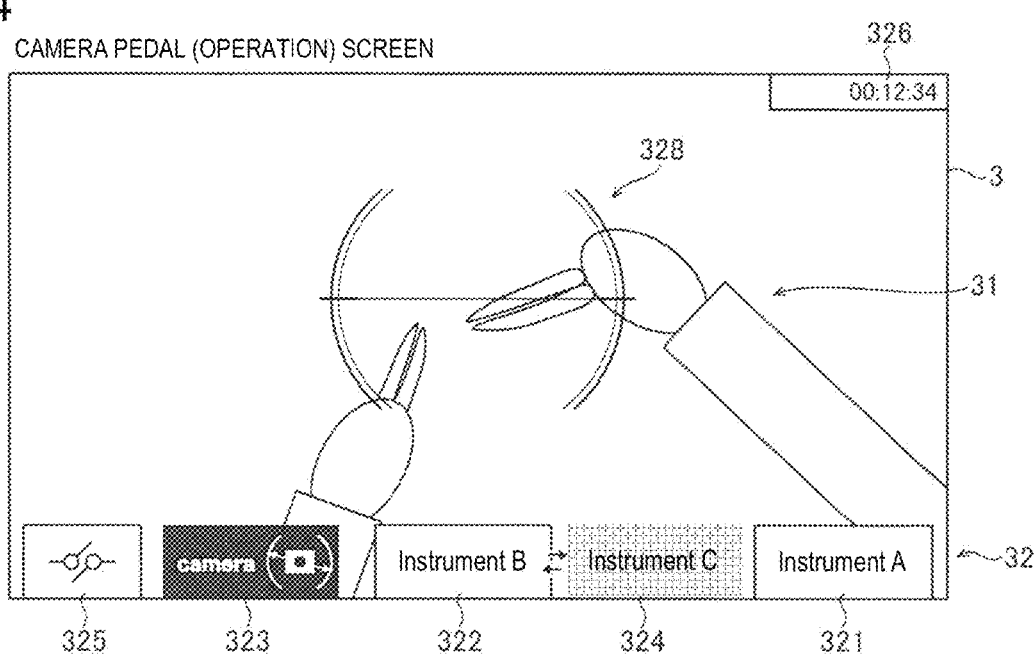
FIG. 14 is a diagram illustrating a view of an example of a screen of the display device when the camera pedal is operated according to an embodiment.

As illustrated in FIG. 14, the level 328 for the endoscope 201d is displayed on the display device 3 when the camera pedal 24 is operated. It is possible to easily change the orientation of the endoscope 201d through operation referring to the level 328.

The control apparatus 6 is configured to change the display form of a corresponding area out of the first area 321, the second area 322, and the third area 323, based on a fact that at least one of the sensors 26 detects setting of the foot of the operator O at the operation preparation position of at least one foot pedal 20 out of the right-side foot pedals (the coagulation pedal 21b and the cutting pedal 22b), the left-side foot pedals (the coagulation pedal 21a and the cutting pedal 22a), and the camera pedal 24.

The changing of the display form of an area includes at least one of display color change, inverted display, display change of the area frame line, and zoom/zoom-out of the display area.

The areas of the graphical user interface 32 are configured to display the operation states of the corresponding foot pedals 20. Thus, the operator O can easily grasp the operation states of the foot pedals 20.

Specifically, in addition to the information on the surgical instrument 201a, the first area 321 displays the information on the right-side foot pedals (the coagulation pedal 21b and the cutting pedal 22b). For example, when the foot of the operator O is set at the operation preparation position of the coagulation pedal 21b or the cutting pedal 22b, the frame line of the first area 321 is displayed with the color of the corresponding foot pedal 20 (the coagulation pedal 21b or the cutting pedal 22b). Thus, the operator O can easily grasp the execution state of the function of the surgical instrument 201a operated by the right-side foot pedals (the coagulation pedal 21b and the cutting pedal 22b) through the display of the first area 321. When the coagulation pedal 21b or the cutting pedal 22b is operated, the first area 321 displays the information on the coagulation pedal 21b or the cutting pedal 22b such that the display is distinguished from that in the case where the foot of the operator O is set at the operation preparation position. For example, when the coagulation pedal 21b or the cutting pedal 22b is operated, the entirety of the first area 321 is displayed with the color of the corresponding foot pedal 20 (the coagulation pedal 21b or the cutting pedal 22b). Thus, the operator O can easily grasp the operation state of the coagulation pedal 21b or the cutting pedal 22b through the display of the first area 321.

In other words, when the coagulation pedal 21b is operated, the first area 321 displays the information on the coagulation pedal 21b. When the cutting pedal 22b is operated, the first area 321 displays the information on the cutting pedal 22b. Consequently, the operator O can easily grasp the execution states of the coagulation function and the cutting function by the surgical instrument 201a that is operated by the right hand-operation handle 1a through the display of the first area 321.

In addition to the information on the surgical instrument 201b, the second area 322 displays the information on the left-side foot pedals (the coagulation pedal 21a and the cutting pedal 22a). For example, when the foot of the operator O is set at the operation preparation position of the coagulation pedal 21a or the cutting pedal 22a, the frame line of the second area 322 is displayed with the color of the corresponding foot pedal 20 (the coagulation pedal 21a or the cutting pedal 22a). Thus, the operator O can easily grasp the execution state of the function of the surgical instrument 201b operated by the left-side foot pedals (the coagulation pedal 21a and the cutting pedal 22a) through the display of the second area 322. When the coagulation pedal 21a or the cutting pedal 22a is operated, the second area 322 displays the information on the coagulation pedal 21a or the cutting pedal 22a such that the display is distinguished from that in the case where the foot of the operator O is set at the operation preparation position. For example, when the coagulation pedal 21a or the cutting pedal 22a is operated, the entirety of the second area 322 is displayed with the color of the corresponding foot pedal 20 (the coagulation pedal 21a or the cutting pedal 22a). Thus, the operator O can easily grasp the operation state of the coagulation pedal 21a or the cutting pedal 22a through the display of the second area 322.

In other words, when the coagulation pedal 21a is operated, the second area 322 displays the information on the coagulation pedal 21a. When the cutting pedal 22a is operated, the second area 322 displays the information on the cutting pedal 22a. Consequently, the operator O can easily grasp the execution states of the coagulation function and the cutting function by the surgical instrument 201b that is operated by the left hand-operation handle 1b through the display of the second area 322.

In addition to the information on the endoscope 201d, the third area 323 displays the information on the camera pedal 24. For example, when the foot of the operator O is set at the operation preparation position of the camera pedal 24, the frame line of the third area 323 is emphasized. Thus, the operator O can easily grasp the execution state of the function of the endoscope 201d operated by the camera pedal 24 through the display of the third area 323. When the camera pedal 24 is operated, the third area 323 displays the information on the camera pedal 24 such that the display is distinguished from that in the case where the foot of the operator O is set at the operation preparation position. For example, when the camera pedal 24 is operated, the background color and the text color of the third area 323 are inverted. Thus, the operator O can easily grasp the operation state of the camera pedal 24 through the display of the third area 323.

Next, with reference to FIGS. 8 to 21, an example of the graphical user interface 32 displayed based on the operation of the foot pedals 20 by the operator O.

Figure 8:
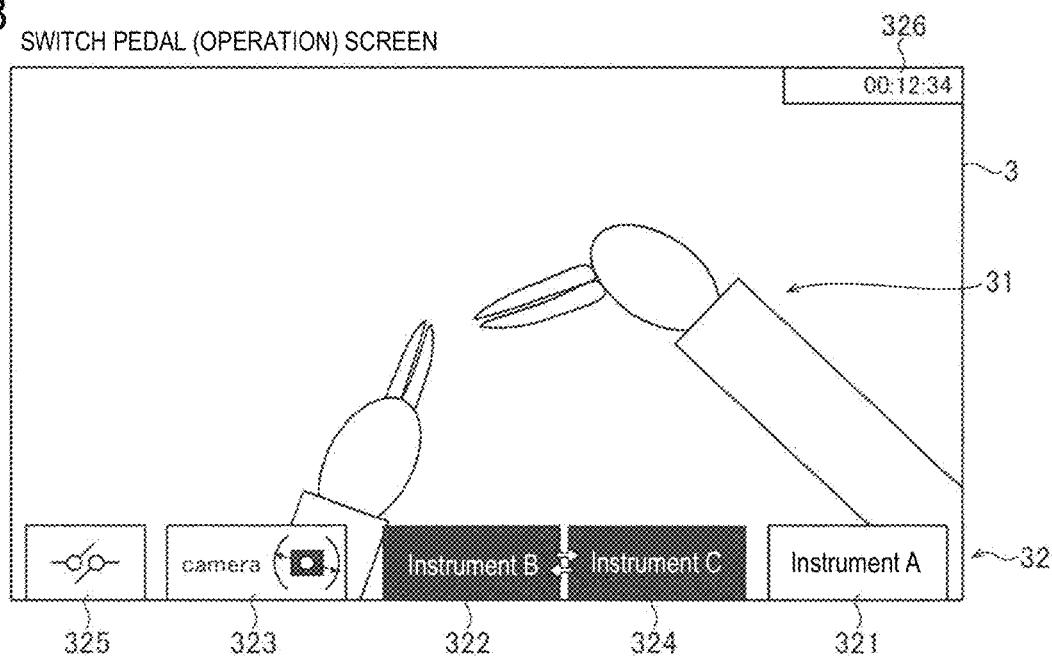
FIG. 8 is a diagram illustrating a view of an example of a screen of the display device when a switch pedal is operated according to an embodiment.

As illustrated in FIG. 8, when the switch pedal 25 is operated, the surgical instrument operated by the left hand-operation handle 1b is switched from the surgical instrument 201b to the surgical instrument 201c. In this case, the background colors and the text colors of the second area 322 and the fourth area 324 are inverted. Thus, the operator O can easily recognize the switching of the surgical instruments.

As illustrated in FIG. 9, when the foot of the operator O is set at the operation preparation position of the clutch pedal 23, the frame line of the fifth area 325 is emphasized. The information on the clutch pedal 23 is popped up and displayed in the pop-up area 327a. Even when the foot of the operator O continues to be set at the operation preparation position of the clutch pedal 23, the display of the pop-up area 327a ends after a lapse of the predetermined time. In this case, the emphasized display of the frame line of the fifth area 325 continues.

Figure 10:
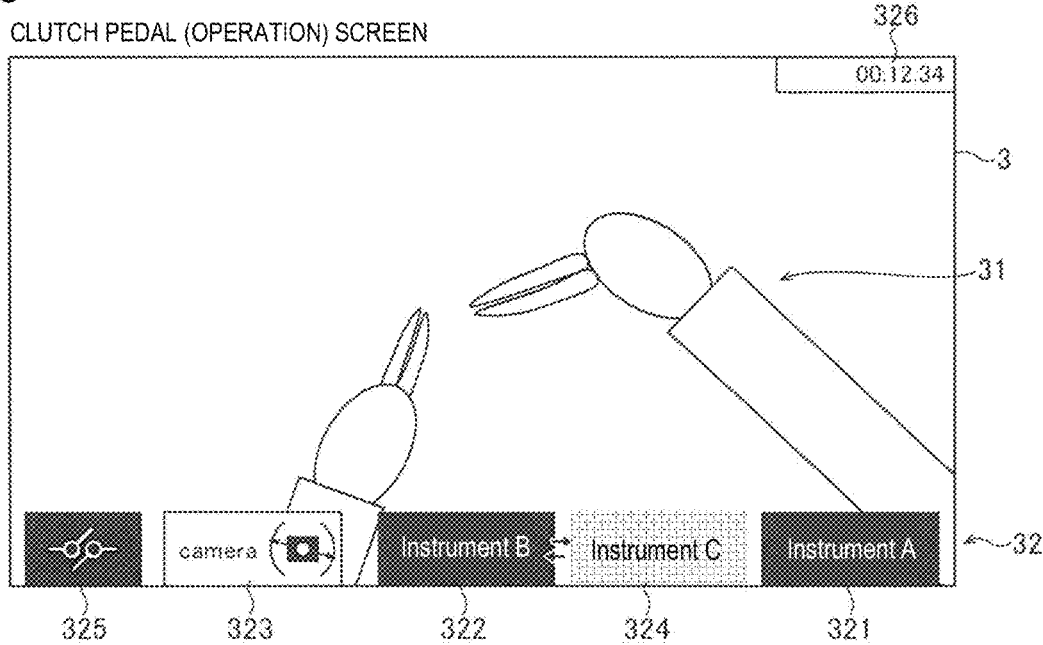
FIG. 10 is a diagram illustrating a view of an example of a screen of the display device when the clutch pedal is operated according to an embodiment.

As illustrated in FIG. 10, when the clutch pedal 23 is operated, the control-related connections between the operation handles 1 and the manipulators 201 are temporarily disconnected. In this case, the background color and the text color of the fifth area 325 displaying the information on the clutch pedal 23 are inverted. Additionally, the background color and the text color of the first area 321 displaying the information on the surgical instrument 201a in which the control-related connection is temporarily disconnected are inverted. Moreover, the background color and the text color of the second area 322 displaying the information on the surgical instrument 201b in which the control-related connection is temporarily disconnected are inverted. When the foot of the operator O goes back to the operation preparation position after the operation, the frame line of the fifth area 325 is emphasized as illustrated in FIG. 9.

Figure 11:
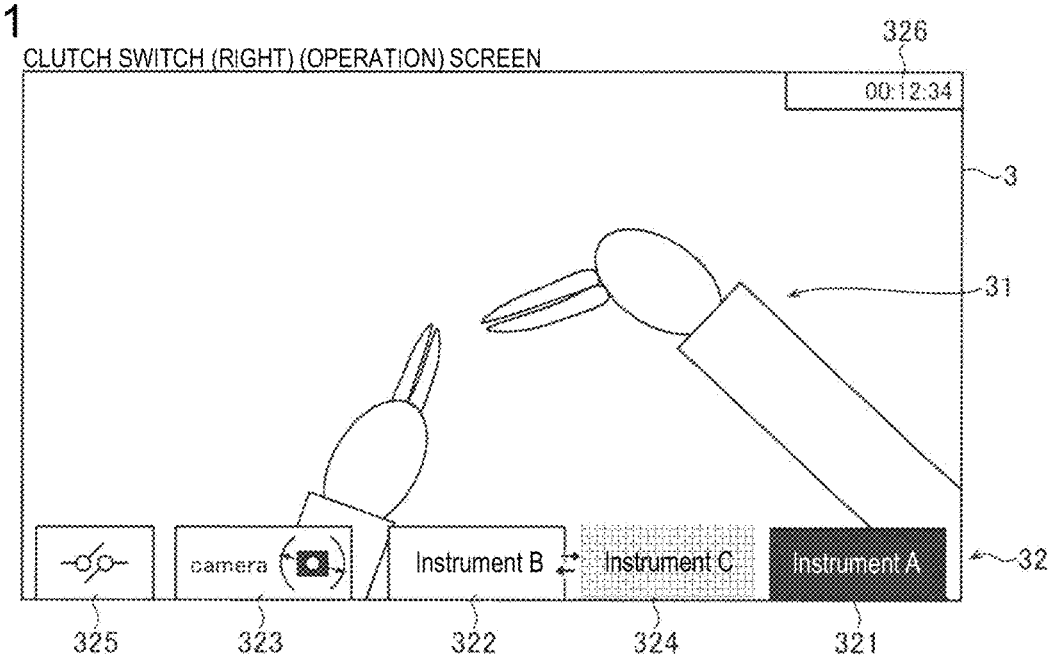
FIG. 11 is a diagram illustrating a view of an example of a screen of the display device when a clutch switch (right) is operated according to an embodiment.

As illustrated in FIG. 11, when the clutch switch 11 of the right hand-operation handle 1a is operated, the control-related connection between the operation handle 1a and the manipulator 201 provided with the surgical instrument 201a is temporarily disconnected. In this case, the background color and text color of the first area 321 displaying the information on the surgical instrument 201a in which the control-related connection is temporarily disconnected are inverted.

Figure 12:
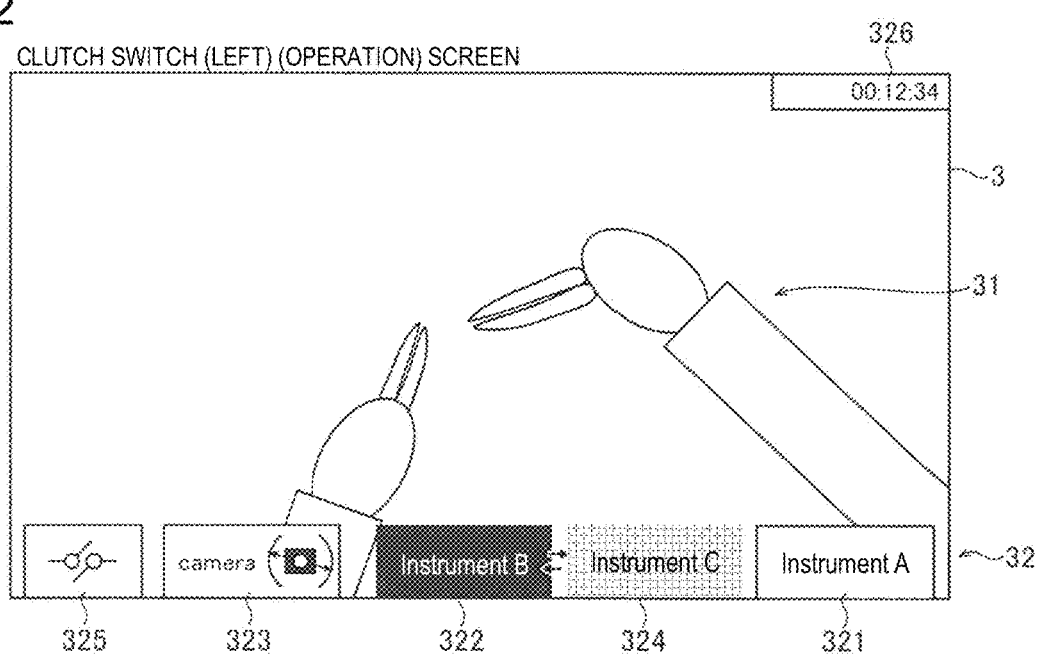
FIG. 12 is a diagram illustrating a view of an example of a screen of the display device when a clutch switch (left) is operated according to an embodiment.

As illustrated in FIG. 12, when the clutch switch 11 of the left hand-operation handle 1b is operated, the control-related connection between the operation handle 1b and the manipulator 201 provided with the surgical instrument 201b is temporarily disconnected. In this case, the background color and the text color of the second area 322 displaying the information on the surgical instrument 201b in which the control-related connection is temporarily disconnected are inverted.

As illustrated in FIG. 13, when the foot of the operator O is set at the operation preparation position of the camera pedal 24, the frame line of the third area 323 is emphasized. Additionally, the information on the camera pedal 24 is popped up and displayed in the pop-up area 327b. Even when the foot of the operator O continues to be set at the operation preparation position of the camera pedal 24, the display of the pop-up area 327b ends after a lapse of the predetermined time. In this case, the emphasized display of the frame line of the third area 323 continues.

As illustrated in FIG. 14, when the camera pedal 24 is operated, the position and orientation of the endoscope 201d can be controlled by the operation handles 1a and 1b. In this process, the background color and the text color of the third area 323 displaying the information on the camera pedal 24 are inverted. Additionally, the level 328 for the endoscope 201d is displayed in the central area.

As illustrated in FIG. 15, when the foot of the operator O is set at the operation preparation position of the cutting pedal 22b corresponding to the surgical instrument 201a being operated by the right hand, the frame line of the first area 321 is emphasized. Specifically, more than left half of the frame line is emphasized by the second color of the cutting pedal 22b. The rest of the frame line is emphasized by the first color of the coagulation pedal 21b. Thus, comparing with a case where the frame line is emphasized by only the second color, the operator O can more effectively recognize setting of the foot at the operation preparation position of the cutting pedal 22b out of the cutting pedal 22b and the coagulation pedal 21b. Additionally, the information on the cutting pedal 22b is popped up and displayed in the pop-up area 327c. Even when the foot of the operator O continues to be set at the operation preparation position of the cutting pedal 22b, the display of the pop-up area 327c ends after a lapse of the predetermined time. In this case, the emphasized display of the frame line of the first area 321 continues.

Likewise, the frame line of the second area 322 is emphasized also when the foot of the operator O is set at the operation preparation position of the cutting pedal 22a corresponding to the surgical instrument 201b being operated by the left hand.

As illustrated in FIG. 16, when the cutting pedal 22b is operated, predetermined voltage is applied to the surgical instrument 201a to enable cutting of the surgery site. In this process, the background of the first area 321 displaying the information on the cutting pedal 22b is displayed with the second color of the cutting pedal 22b.

Likewise, also when the cutting pedal 22a is operated, the background of the second area 322 displaying the information on the cutting pedal 22a is displayed with the second color of the cutting pedal 22a.

As illustrated in FIG. 17, when the foot of the operator O is set at the operation preparation position of the coagulation pedal 21b corresponding to the surgical instrument 201a being operated by the right hand, the frame line of the first area 321 is emphasized. Specifically, more than right half of the frame line is emphasized by the first color of the coagulation pedal 21b. The rest of the frame line is emphasized by the second color of the cutting pedal 22b. Thus, comparing with a case where the frame line is emphasized by only the first color, the operator O can more effectively recognize setting of the foot at the operation preparation position of the coagulation pedal 21b out of the cutting pedal 22b and the coagulation pedal 21b. Additionally, the information on the coagulation pedal 21b is popped up and displayed in the pop-up area 327d. Even when the foot of the operator O continues to be set at the operation preparation position of the coagulation pedal 21b, the display of the pop-up area 327d ends after a lapse of the predetermined time. In this case, the emphasized display of the frame line of the first area 321 continues.

Likewise, the frame line of the second area 322 is emphasized also when the foot of the operator O is set at the operation preparation position of the coagulation pedal 21a corresponding to the surgical instrument 201b being operated by the left hand.

Figure 18:
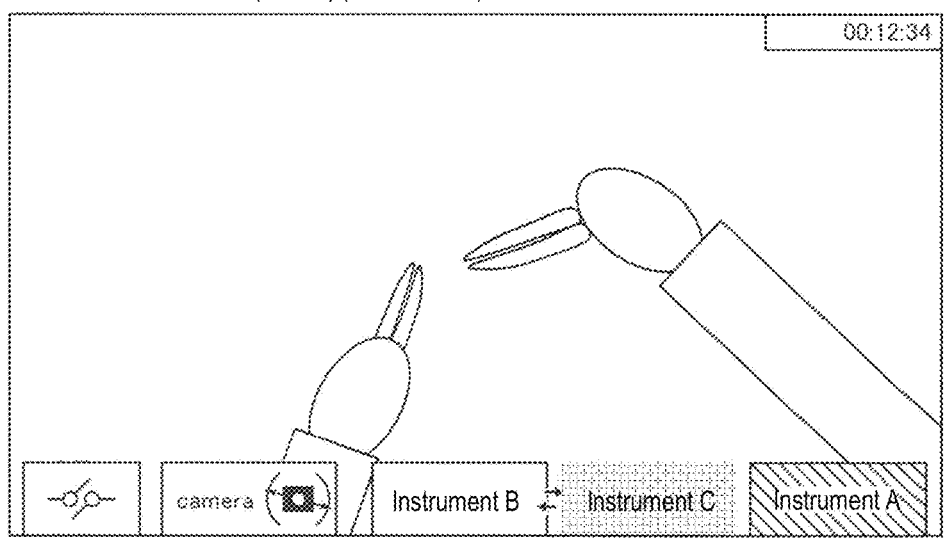
FIG. 18 is a diagram illustrating a view of an example of a screen of the display device when the coagulation pedal (right) is operated according to an embodiment.

As illustrated in FIG. 18, when the coagulation pedal 21b is operated, predetermined voltage is applied to the surgical instrument 201a to enable cutting of the surgery site. In this process, the background of the first area 321 displaying the information on the coagulation pedal 21b is displayed with the first color of the coagulation pedal 21b.

Likewise, also when the coagulation pedal 21a is operated, the background of the second area 322 displaying the information on the coagulation pedal 21a is displayed with the first color of the coagulation pedal 21a.

Figure 19:
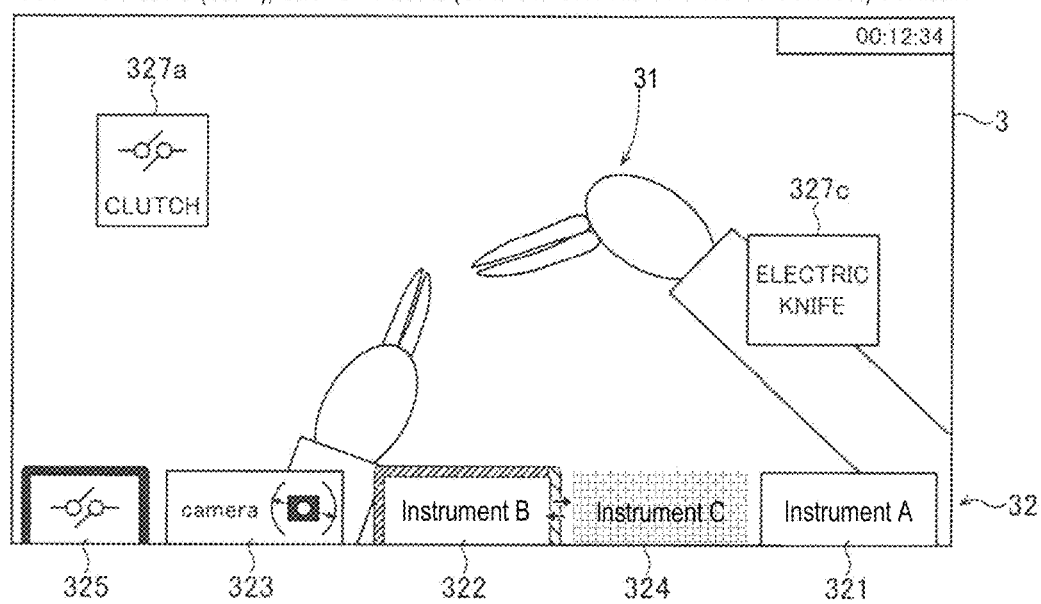
FIG. 19 is a diagram illustrating a view of an example of a screen of the display device when feet are at operation preparation positions for a cutting pedal (left) and the clutch pedal according to an embodiment.

As illustrated in FIG. 19, when the foot of the operator O is set at the operation preparation position of the cutting pedal 22a corresponding to the surgical instrument 201b being operated by the left hand and the other foot of the operator O is set at the operation preparation position of the clutch pedal 23, the frame line of the second area 322 is emphasized. Specifically, more than left half of the frame line is emphasized by the second color of the cutting pedal 22a. The rest of the frame line is emphasized by the first color of the coagulation pedal 21a. Additionally, the information on the cutting pedal 22a is popped up and displayed in the pop-up area 327c. Moreover, the frame line of the fifth area 325 is emphasized. The information on the clutch pedal 23 is popped up and displayed in the pop-up area 327a.

Figure 20:
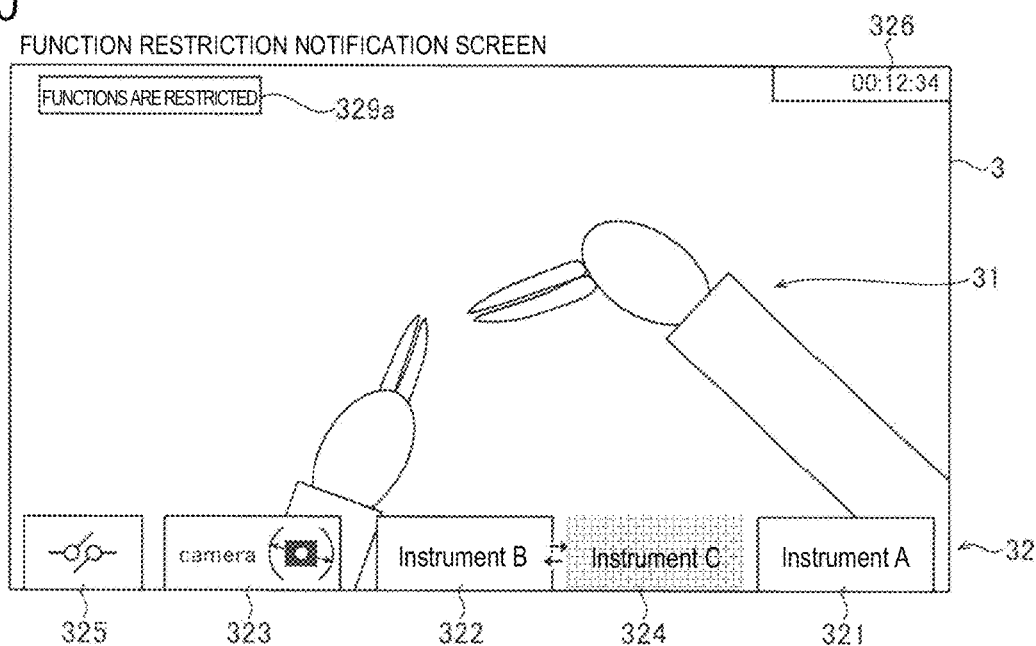
FIG. 20 is a diagram illustrating a view of an example of a screen of the display device on which a function limit notification is displayed according to an embodiment.

As illustrated in FIG. 20, when the functions are restricted, a notification to indicate that the functions are restricted is displayed in the error notification area 329a. When the cutting pedals 22 and the coagulation pedals 21 are operated while a surgical instrument in which the functions of cutting and coagulating are not set, a notification to indicate that unfunctional operation is tried to be executed is popped up and displayed on the upper side of the area corresponding to the surgical instrument. In this case, no voltage is applied to the surgical instrument even if the cutting pedals 22 and the coagulation pedals 21 are operated.

Figure 21:
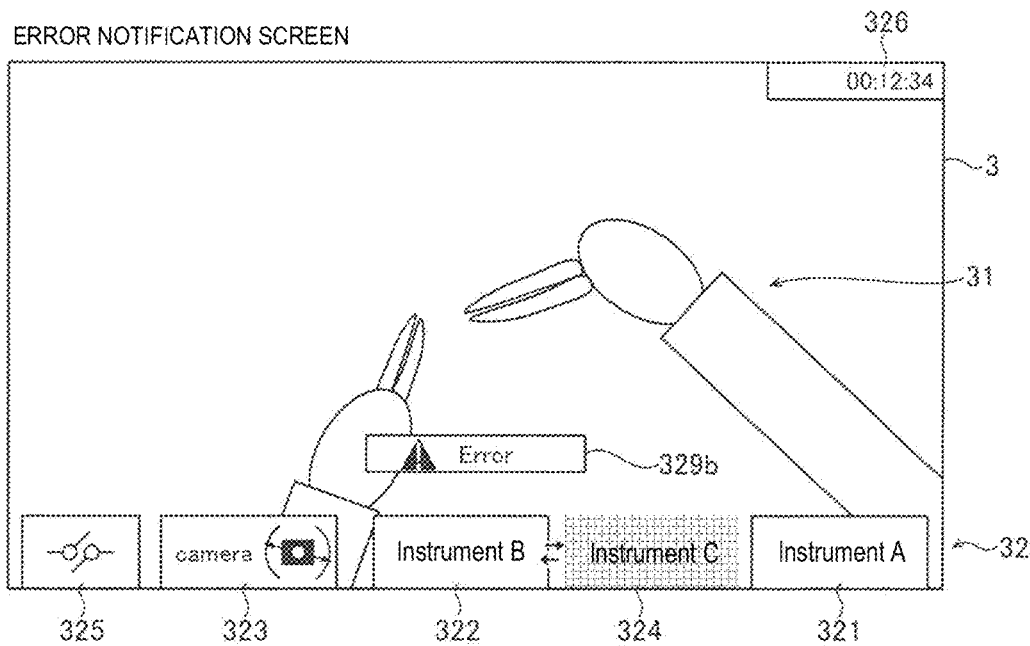
FIG. 21 is a diagram illustrating a view of an example of a screen of the display device on which an error notification is displayed according to an embodiment.

As illustrated in FIG. 21, when an error is notified, the error notification is displayed in the error notification area 329b.

Modifications

The one or more embodiments disclosed above should be construed as an example in all aspects and should not limit the invention. The scope of the invention is indicated by the scope of claim instead of by the above-described one or more embodiments.

For example, the foot pedals on the operation pedal section include the coagulation pedals and the cutting pedals in the example illustrated in the above-described one or more embodiments, but the invention is not limited thereto. In an embodiment or a modification, the foot pedals on the operation pedal section may include a foot pedal that executes a function of medical equipment other than the coagulation pedals and the cutting pedals.

The sensor is the blockage type in the example illustrated in the above-described one or more embodiments, but the invention is not limited thereto. The sensor may be a transparent type or a reflection type. Otherwise, the sensor may detect the presence of the foot without using light. For example, the detection may be performed by using a soundwave or a coil. The sensor is not limited to the contactless type and may detect the presence of the foot by contact. For example, the sensor may be a mechanical switch.

The invention claimed is:

1. A surgical system, comprising:
a first manipulator that supports a first surgical instrument;
a second manipulator that supports a second surgical instrument;
a third manipulator that supports an endoscope;
an operation apparatus that includes a display device that displays an endoscopic image captured by the endoscope on an entirety of a screen of the display device, a first operation handle to be operated by right hand, and a second operation handle to be operated by left hand; and
a control apparatus that controls at least the display device, wherein
the control apparatus displays, on the entirety of the screen of the display device, the endoscopic image captured by the endoscope, and displays on a portion of the screen of the display device, a graphical user interface in superimposed relation with the display of the endoscopic image captured by the endoscope, and
when the endoscope is moved by the third manipulator, the control apparatus displays the graphical user interface, which comprises a level for the endoscope in a central area other than a lower end region and an upper end region of the screen of the display device, wherein the level is displayed on a portion of the screen of the display device in superimposed relation with the endoscopic image displayed on the entirety of the screen of the display device, and
when the endoscope is not moved by the third manipulator, the control apparatus displays the graphical user interface, without including the level for the endoscope displayed in superimposed relation with the endoscopic image displayed on the entirety of the screen.

2. The surgical system according to claim 1, wherein
the first surgical instrument is operated by the first operation handle, the second surgical instrument is operated by the second operation handle, and the endoscope is configured to move by operating both the first and second operation handles.

3. The surgical system according to claim 1, wherein
the graphical user interface includes a first area that displays information on the first surgical instrument, a second area that displays information on the second surgical instrument, and a third area that displays information on the endoscope in the lower end region or in the upper end region of the display device.

4. The surgical system according to claim 3, wherein
the first area displays a type of the first surgical instrument, and
the second area displays a type of the second surgical instrument.

5. The surgical system according to claim 3, wherein
the graphical user interface arranges the first area, the second area, and the third area in order from right to left.

6. The surgical system according to claim 3, further comprising:
a fourth manipulator that supports a replacement surgical instrument, wherein
the graphical user interface includes a fourth area that is arranged between the first area and the second area and displays information on the replacement surgical instrument.

7. The surgical system according to claim 1, further comprising:
a patient-side apparatus including a platform that supports the first, second and third manipulators.

8. The surgical system according to claim 1, wherein
the operation apparatus further includes an operation pedal section that includes a first pedal to execute a function of the first surgical instrument, a second pedal to execute a function of the second surgical instrument, and a third pedal for causing the first and second operation handles to execute a function of moving the endoscope.

9. The surgical system according to claim 8, wherein
the moving the endoscope is executed by the first and second operation handles when the third pedal is operated.

10. The surgical system according to claim 8, wherein
the control apparatus displays the level when the third pedal is operated.

11. A surgical system, comprising:
a first manipulator that supports a first surgical instrument;
a second manipulator that supports a second surgical instrument;
a third manipulator that supports an endoscope;
an operation apparatus that includes a display device that displays an endoscopic image captured by the endoscope, and first and second operation handles for operating the first to third manipulators; and
a control apparatus that controls at least the display device, wherein
the control apparatus displays, on the display device, a graphical user interface in superimposed relation with the endoscopic image, and
when the endoscope is moved by the third manipulator, the control apparatus displays the graphical user interface, which comprises a level for the endoscope in a central area other than a lower end region and an upper end region of the display device, wherein the level is in superimposed relation with the endoscopic image, and
when the endoscope is not moved by the third manipulator, the control apparatus displays the graphical user interface, without including the level for the endoscope displayed in superimposed relation with the endoscopic image displayed on the entirety of the screen.

12. The surgical system according to claim 11, wherein
the graphical user interface includes a first area that displays information on the first surgical instrument, a second area that displays information on the second surgical instrument, and a third area that displays information on the endoscope in the lower end region or in the upper end region of the display device.

13. The surgical system according to claim 12, wherein
the first area displays a type of the first surgical instrument, and
the second area displays a type of the second surgical instrument.

14. The surgical system according to claim 12, wherein
the graphical user interface arranges the first area, the second area, and the third area in order from right to left.

15. The surgical system according to claim 12, further comprising:
a fourth manipulator that supports a replacement surgical instrument, wherein
the graphical user interface includes a fourth area that is arranged between the first area and the second area and displays information on the replacement surgical instrument.

16. The surgical system according to claim 11, further comprising:
a patient-side apparatus including a platform that supports the first, second and third manipulators.

17. The surgical system according to claim 11, wherein
the first surgical instrument is operated by the first operation handle, the second surgical instrument is operated by the second operation handle, and the endoscope is configured to move by operating both the first and second operation handles.

18. The surgical system according to claim 11, wherein
the operation apparatus further includes an operation pedal section that includes a first pedal to execute a function of the first surgical instrument, a second pedal to execute a function of the second surgical instrument, and a third pedal for causing the first and second operation handles to execute a function of moving the endoscope.

19. The surgical system according to claim 18, wherein
the moving the endoscope is executed by the first and second operation handles when the third pedal is operated.

20. The surgical system according to claim 18, wherein
the control apparatus displays the level when the third pedal is operated.

* * * * *